US008983682B1

(12) United States Patent
Peeters et al.

(10) Patent No.: US 8,983,682 B1
(45) Date of Patent: Mar. 17, 2015

(54) UNLOCKING MOBILE-DEVICE AND/OR UNMANNED AERIAL VEHICLE CAPABILITY IN AN EMERGENCY SITUATION

(71) Applicants: Eric Peeters, Mountain View, CA (US); Eric Teller, Palo Alto, CA (US); William Graham Patrick, San Francisco, CA (US)

(72) Inventors: Eric Peeters, Mountain View, CA (US); Eric Teller, Palo Alto, CA (US); William Graham Patrick, San Francisco, CA (US)

(73) Assignee: Google Inc., Mountain View, CA (US)

( * ) Notice: Subject to any disclaimer, the term of this patent is extended or adjusted under 35 U.S.C. 154(b) by 305 days.

(21) Appl. No.: 13/730,189

(22) Filed: Dec. 28, 2012

(51) Int. Cl.
| | |
|---|---|
| *G05D 1/12* | (2006.01) |
| *G05D 1/10* | (2006.01) |
| *B64C 39/02* | (2006.01) |
| *B64C 29/00* | (2006.01) |
| *B64C 19/00* | (2006.01) |
| *G05D 1/00* | (2006.01) |
| *B64C 27/20* | (2006.01) |
| *B64C 27/26* | (2006.01) |

(52) U.S. Cl.
CPC ............. *B64C 39/024* (2013.01); *B64C 19/00* (2013.01); *B64C 29/0025* (2013.01); *B64C 27/20* (2013.01); *B64C 27/26* (2013.01); *B64C 2201/146* (2013.01); *G05D 1/0011* (2013.01); *B64C 2201/126* (2013.01)
USPC .................................. 701/2; 701/3; 244/190

(58) Field of Classification Search
None
See application file for complete search history.

(56) References Cited

U.S. PATENT DOCUMENTS

| | | | |
|---|---|---|---|
| 5,311,197 A * | 5/1994 | Sorden et al. ................. | 342/457 |
| 6,056,237 A | 5/2000 | Woodland | |
| 6,567,044 B2 | 5/2003 | Carroll | |
| 6,817,573 B2 | 11/2004 | Harrison et al. | |
| 6,965,816 B2 | 11/2005 | Walker | |
| 7,574,193 B2 | 8/2009 | Hulkkonen et al. | |
| 7,813,888 B2 | 10/2010 | Vian et al. | |
| 7,877,785 B2 | 1/2011 | Selignan | |
| 8,028,952 B2 | 10/2011 | Urnes, Sr. | |
| 2006/0167597 A1 * | 7/2006 | Bodin et al. ...................... | 701/3 |
| 2007/0049251 A1 | 3/2007 | Mock et al. | |
| 2008/0085732 A1 | 4/2008 | Mizuide et al. | |
| 2009/0050750 A1 * | 2/2009 | Goossen ...................... | 244/76 R |
| 2010/0084513 A1 | 4/2010 | Gariepy et al. | |

(Continued)

OTHER PUBLICATIONS

Mitchell J.H. Lum, et al., Telesurgery Via Unmanned Aerial Vehicle (UAV) with a Field Deployable Surgical Robot, Medicine Meets Virtual Reality 15, Feb. 2007, Long Beach, California.

(Continued)

*Primary Examiner* — Michael J Zanelli
(74) *Attorney, Agent, or Firm* — McDonnell Boehnen Hulbert & Berghoof LLP

(57) ABSTRACT

An illustrative emergency-support system may include multiple unmanned aerial vehicles (UAVs), which are configured to provide emergency support for a number of different emergency situations. Further, the emergency-support system may be configured to: (a) identify a request for assistance in a remote emergency situation, (b) identify a remote device associated with the request for assistance, (c) determine a target location corresponding to the emergency situation, (d) control a UAV to travel to the target location to provide emergency support, and (e) enable an otherwise restricted capability of one or more of the remote device or the UAV after controlling the UAV to travel to the target location, wherein the capability is enabled to help provide emergency support in the remote emergency situation.

23 Claims, 6 Drawing Sheets

(56) References Cited

U.S. PATENT DOCUMENTS

| | | |
|---|---|---|
| 2010/0256839 A1 | 10/2010 | Fitzpatrick |
| 2010/0280699 A1 | 11/2010 | Bageshwar et al. |
| 2011/0084162 A1 | 4/2011 | Goossen et al. |
| 2011/0128372 A1 | 6/2011 | Malecki et al. |
| 2011/0130636 A1 | 6/2011 | Daniel et al. |
| 2011/0267241 A1 | 11/2011 | Grimm et al. |
| 2011/0281679 A1 | 11/2011 | Larrabee et al. |
| 2011/0315806 A1 | 12/2011 | Piasecki et al. |
| 2012/0080556 A1 | 4/2012 | Root, Jr. |
| 2012/0152654 A1 | 6/2012 | Marcus |
| 2014/0111332 A1* | 4/2014 | Przybylko et al. ......... 340/539.1 |

OTHER PUBLICATIONS

H.S. Nguyen, et al., Situation Identification by Unmanned Aerial Vehicle, Institute of Mathematics, 2001, pp. 49-56, Warsaw University.

Elizabeth Bone et al., Unmanned Aerial Vehicles: Background and Issues for Congress, Report for Congress, Congressional Research Service, The Library of Congress, Apr. 25, 2003.

\* cited by examiner

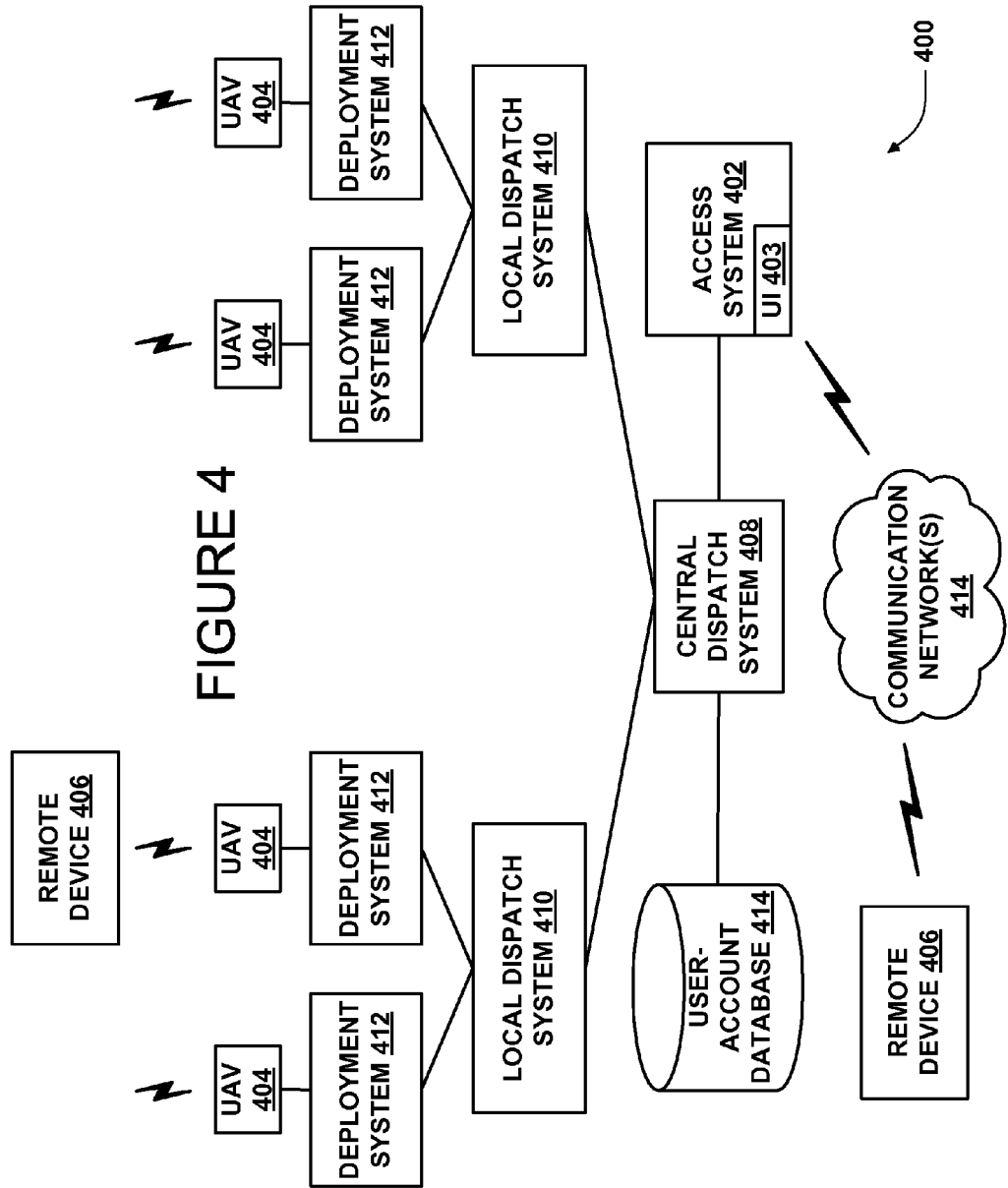

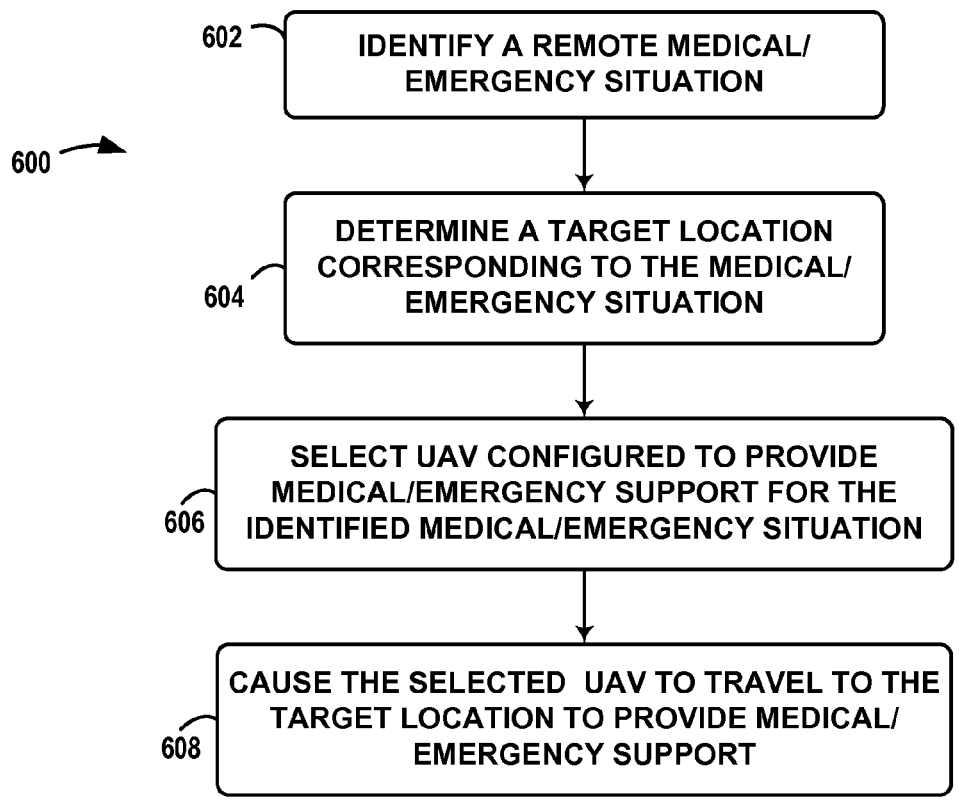
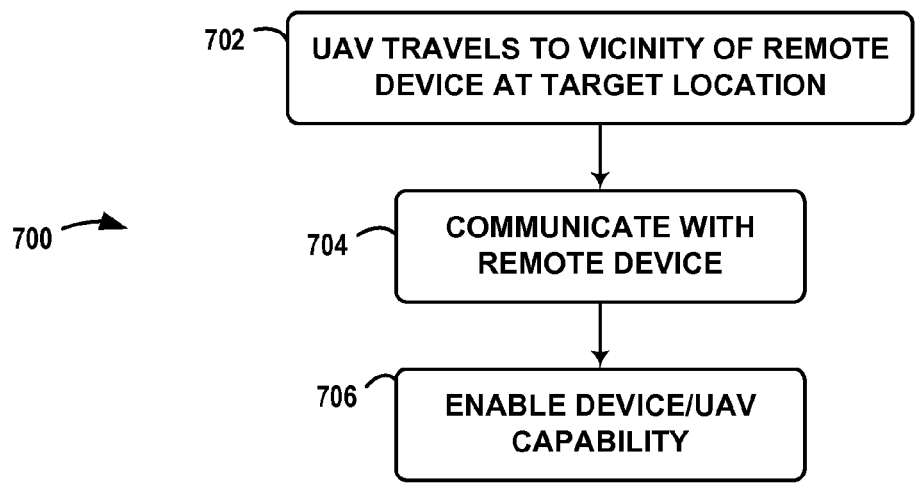

UNLOCKING MOBILE-DEVICE AND/OR UNMANNED AERIAL VEHICLE CAPABILITY IN AN EMERGENCY SITUATION

BACKGROUND

Unless otherwise indicated herein, the materials described in this section are not prior art to the claims in this application and are not admitted to be prior art by inclusion in this section.

An unmanned vehicle, which may also be referred to as an autonomous vehicle, is a vehicle capable of travel without a physically-present human operator. An unmanned vehicle may operate in a remote-control mode, in an autonomous mode, or in a partially autonomous mode.

When an unmanned vehicle operates in a remote-control mode, a pilot or driver that is at a remote location can control the unmanned vehicle via commands that are sent to the unmanned vehicle via a wireless link. When the unmanned vehicle operates in autonomous mode, the unmanned vehicle typically moves based on pre-programmed navigation waypoints, dynamic automation systems, or a combination of these. Further, some unmanned vehicles can operate in both a remote-control mode and an autonomous mode, and in some instances may do so simultaneously. For instance, a remote pilot or driver may wish to leave navigation to an autonomous system while manually performing another task, such as operating a mechanical system for picking up objects, as an example.

Various types of unmanned vehicles exist for various different environments. For instance, unmanned vehicles exist for operation in the air, on the ground, underwater, and in space. Unmanned vehicles also exist for hybrid operations in which multi-environment operation is possible. Examples of hybrid unmanned vehicles include an amphibious craft that is capable of operation on land as well as on water or a floatplane that is capable of landing on water as well as on land. Other examples are also possible.

SUMMARY

In one aspect, a computer-implemented method includes identifying, at a computing device, a request for assistance at a remote emergency situation. The request being associated with a remote device. The method further includes identifying the remote device associated with the request for assistance, determining a target location corresponding to the emergency situation, and controlling an unmanned aerial vehicle (UAV) to travel to the target location to provide emergency support. The UAV can be selected from a plurality of UAVs that are configured to provide emergency support for a plurality of emergency situations and the selection of the UAV can be based at least in part on a determination that the selected UAV is configured for the identified emergency situation. Further, the method includes enabling an otherwise restricted capability of one or more of the remote device or the UAV after controlling the UAV to travel to the target location. The capability is enabled to help provide emergency support in the remote emergency situation.

In a further aspect, a non-transitory computer readable medium has stored therein instructions that are executable to cause a computing device to perform functions that include identifying a request for assistance at a remote emergency situation and identifying a remote device that is associated with the request for assistance. The functions also include determining a target location corresponding to the emergency situation and controlling an unmanned aerial vehicle (UAV) to travel to the target location to provide emergency support. The UAV can be selected from a plurality of UAVs that are configured to provide emergency support for a plurality of emergency situations and the selection of the UAV can be based at least in part on a determination that the selected UAV is configured for the identified emergency situation. Further, the functions include enabling an otherwise restricted capability of one or more of the remote device or the UAV after controlling the UAV to travel to the target location. The capability is enabled to help provide emergency support in the remote emergency situation.

In another aspect, an emergency-support system includes a plurality of unmanned aerial vehicles (UAVs). The plurality of UAVs is configured to provide emergency support for a plurality of emergency situations. The system also includes at least one component that is configured to identify a request for assistance at a remote emergency situation and identify a remote device that is associated with the request for assistance. The at least one component if also configured to determine a target location corresponding to the emergency situation and control an unmanned aerial vehicle (UAV) to travel to the target location to provide emergency support. The UAV can be selected from a plurality of UAVs that are configured to provide emergency support for a plurality of emergency situations and the selection of the UAV can be based at least in part on a determination that the selected UAV is configured for the identified emergency situation. Further, the at least one component is configured to enable an otherwise restricted capability of one or more of the remote device or the UAV after controlling the UAV to travel to the target location. The capability is enabled to help provide emergency support in the remote emergency situation.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 4 is a simplified block diagram illustrating a medical-support system, according to an example embodiment.

FIG. 6 is a flowchart illustrating a method according to an example embodiment.

FIG. 7 is a flowchart illustrating a method according to an example embodiment.

DETAILED DESCRIPTION

Figure 1:
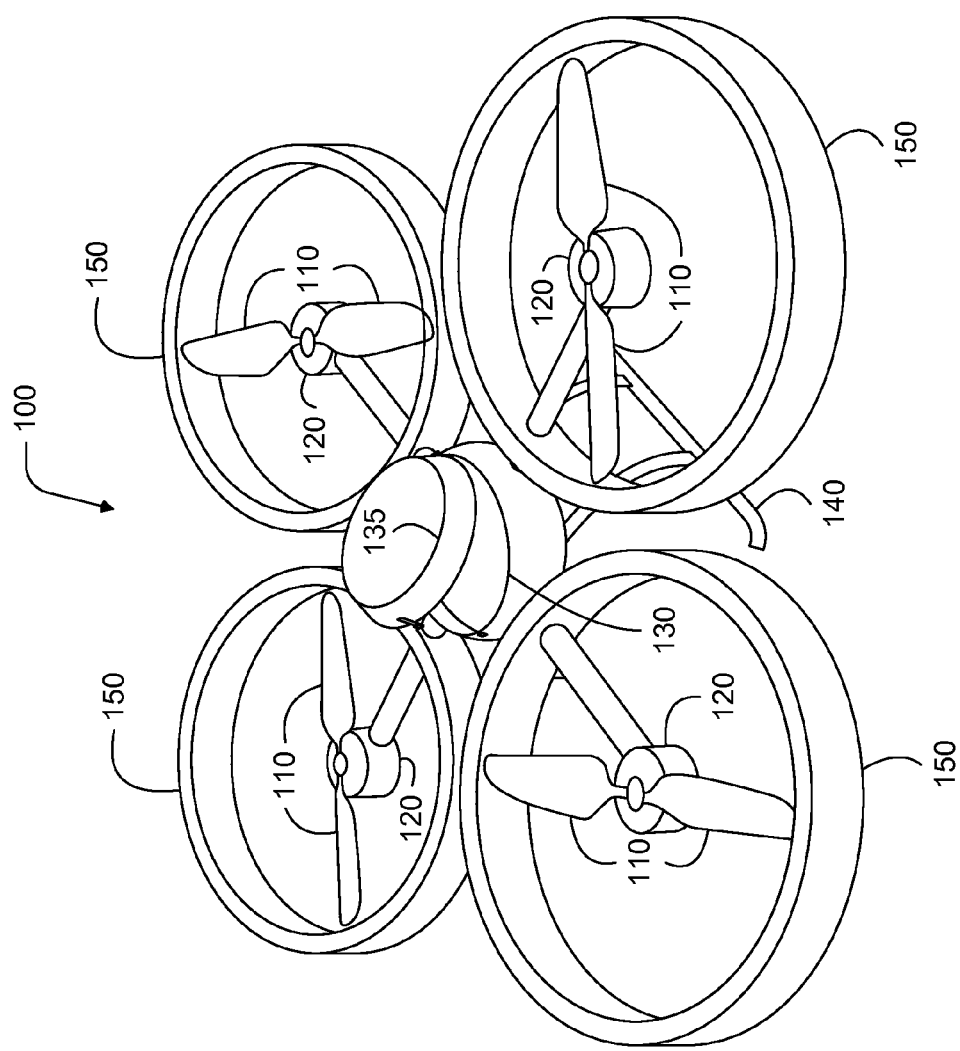
FIGS. 1, 2, 3A, and 3B are simplified illustrations of unmanned aerial vehicles, according to example embodiments.

Exemplary methods and systems are described herein. It should be understood that the word "exemplary" is used herein to mean "serving as an example, instance, or illustration." Any embodiment or feature described herein as "exemplary" or "illustrative" is not necessarily to be construed as preferred or advantageous over other embodiments or features. More generally, the embodiments described herein are not meant to be limiting. It will be readily understood that certain aspects of the disclosed systems and methods can be arranged and combined in a wide variety of different configurations, all of which are contemplated herein.

I. Overview

Embodiments described herein may relate to and/or may be implemented in a system in which unmanned vehicles, and in particular, "unmanned aerial vehicles" (UAVs), are configured to provide medical or other emergency support.

In an illustrative embodiment, a medical-support system may include a fleet of UAVs that are distributed throughout a geographic area, such as a city. The medical-support system may be configured for communications with remote or mobile devices, such as mobile phones or other handheld computer, so that medical support can be requested by a person in need of such medical support (or by others on behalf of a person in need). The medical-support system can then dispatch the appropriate UAV or UAVs to the scene of the medical situation in order to provide medical support.

In particular, a medical-support system may include a fleet with a number of different types of UAVs, which are configured for different medical situations. For instance, some medical emergency UAVs may be configured with items and/or functionality that are expected to be helpful in a cardiac-arrest situation, some UAVs may be configured to help a choking victim, some UAVs may be configured to help a trauma victim, and so on. As such, an illustrative medical-support system may be configured to identify or classify the particular type of medical situation that is occurring, to select the appropriate UAV from those that are available, and to dispatch the selected UAV to the scene of the medical situation.

In a further aspect, a medical-support system may be configured to locate where the medical situation is occurring or has occurred, so that one or more selected UAVs can be dispatched to the location. Further, once the location of the medical situation has been determined, the medical-support system may configure the selected UAV or UAVs to autonomously navigate to (or at least near to) the location of the medical situation. In some embodiments, the medical-support system may configure a UAV to travel to a general location near the scene of medical situation, at which point the medical-support system may provide for remote control of the UAV by an operator, so the operator can manually navigate the UAV to the specific location of the medical situation (e.g., to a specific person in a crowded market).

An illustrative medical-support system may also be configured to enable or unlock an otherwise restricted capability of a UAV and/or another remote computing device in response to receiving a request for medical support. In one example, the medical-support system may unlock a restricted capability of a remote device, such as a mobile device that requested medical support from the scene of a medical situation, in response to receiving the request for medical support and dispatching a UAV to provide medical support.

Alternatively or in addition, the medical-support system can be configured to unlock a capability of the UAV and/or the mobile device in response to the UAV arriving within a nearby vicinity of the mobile device. More specifically, when the UAV arrives within a nearby vicinity of the mobile device (e.g., within 50 meters) the UAV can establish a communication link or use a previously established communication link with the mobile device to unlock and/or authorize various capabilities of the mobile device, which may help to provide medical support.

The UAV can be configured for short-range communications to identify and/or authenticate the identity of the particular mobile device that requested the medical support, and/or to unlock capabilities of the mobile device. Such short-range communication may include WiFi, radio frequency identification (RFID), wireless local-area networks (WLANs), and Bluetooth, for example, although other short-range and long-range communication may also be utilized.

The medical-support system may authorize and/or unlock various capabilities, which may generally be useful to provide medical support in a medical situation. Illustratively, the capability or capabilities can include an otherwise restricted communication capability, such as enabling wireless communications in a restricted bandwidth range, enabling wireless communications above a restricted power level or outside a restricted range, and/or granting access to a restricted communication network.

Illustratively, when a request for medical support is made through a remote device, the remote device can be enabled to communicate on an otherwise restricted frequency band and/or above a restricted power level. The communications can be between the remote device and the medical-support system in general or, more particularly, between the remote device and a UAV that has been dispatched to provide medical support. Such communications between the remote device and the UAV can assist the UAV to identify the remote device, to locate the medical situation, or to otherwise provide medical support. Once the UAV arrives within a nearby vicinity of the remote device, the medical-support system can authorize or enable another capability that can be used to further provide medical support.

In one example, a two-way short-range communication capability can be enabled between the mobile device and the UAV. Illustratively, the UAV can serve as a local communication hot spot (e.g., a local area network (LAN) node) and the UAV can grant access to the mobile device to connect to the communication hot spot and perhaps to a broader network to facilitate other communications.

In yet another example, the mobile device can enable a beacon signal that is detectable by the UAV to help the UAV determine the specific location of the medical situation. The beacon signal can be one or more of a radio frequency signal, a light signal, or an audio signal emitted by the mobile device. The beacon signal can then be used by the UAV to determine the location of the mobile device, which may correspond to the location of the medical situation or to a user of the device that can help direct the UAV to the location of the medical situation.

The UAV could also authorize access to otherwise-restricted information, such as medical histories or other private or sensitive data, if the person or persons to whom such information relates have given permission for such access in a medical situation. Further, the capability can relate to authorizing the UAV to provide assistance for the medical situation. Illustratively, the authorized assistance can include providing information or instructions to a person at the location of the medical situation, providing access to an item that would be useful to assist in the medical situation, or enabling some other operational function of the UAV.

Further, the enabled or unlocked capability need not be of the computing device that requested the medical support but can be a capability of any other computing device, as well as, any other UAV. Illustratively, the UAV can communicate with a computing device that requested medical support and determine that the UAV is within a nearby vicinity of the computing device. In response, the UAV can authorize use of a separate computing device, perhaps a computing device provided by the UAV itself or other accessible, perhaps nearby, computing devices. Thus, the medical-support system can provide access to specialized medical support through the separate computing device after confirming that the medical support is being provided to an authorized user. The medical-support system can also authorize or enable a first computing device that requested the medical support to utilize a second computing device to improve a computing and/or communication capability of the first computing device.

It should be understood that the above embodiments, and other embodiments described herein, are provided for explanatory purposes, and are not intended to be limiting.

Herein, a "medical situation" should be understood to include any situation to which government or private entity, such as a police department, a fire department, and/or an emergency medical services (EMS) entity, might dispatch its personnel. Therefore, some medical situations may in fact be non-medical in nature. For example, a medical or emergency situation to which a police car, fire truck, or ambulance might be dispatched may be considered a medical situation for purposes of this disclosure. Medical support may not be required at such emergency situations (e.g., when police are sent to the scene of a non-violent crime). Further, some non-emergency situations to which a police car, fire truck, ambulance, or the like might be dispatched, may also be considered a medical situation for purposes of this disclosure. Thus, while exemplary embodiments may be described as being implemented to help provide medical support at the scene of a medical situation, those skilled in the art will understand that the UAVs, the functionality of such UAVs, and/or other aspects of the embodiments that are explicitly described herein can also apply in non-medical and/or non-emergency applications.

II. Illustrative Unmanned Vehicles

The term "unmanned aerial vehicle" or UAV, as used in this disclosure, refers to any autonomous or semi-autonomous vehicle that is capable of performing some functions without a physically-present human pilot. Examples of flight-related functions may include, but are not limited to, sensing its environment or operating in the air without a need for input from an operator, among others.

A UAV may be autonomous or semi-autonomous. For instance, some functions could be controlled by a remote human operator, while other functions are carried out autonomously. Further, a UAV may be configured to allow a remote operator to take over functions that can otherwise be controlled autonomously by the UAV. Yet further, a given type of function may be controlled remotely at one level of abstraction and performed autonomously at another level of abstraction. For example, a remote operator could control high level navigation decisions for a UAV, such as by specifying that the UAV should travel from one location to another (e.g., from the city hall in Palo Alto to the city hall in San Francisco), while the UAV's navigation system autonomously controls more fine-grained navigation decisions, such as the specific route to take between the two locations, specific flight controls to achieve the route and avoid obstacles while navigating the route, and so on. Other examples are also possible.

A UAV can be of various forms. For example, a UAV may take the form of a rotorcraft such as a helicopter or multicopter, a fixed-wing aircraft, a jet aircraft, a ducted fan aircraft, a lighter-than-air dirigible such as a blimp or steerable balloon, a tail-sitter aircraft, a glider aircraft, and/or an ornithopter, among other possibilities. Further, the terms "drone", "unmanned aerial vehicle system" (UAVS), or "unmanned aerial system" (UAS) may also be used to refer to a UAV.

FIG. 1 is a simplified illustration of a UAV, according to an example embodiment. In particular, FIG. 1 shows an example of a rotorcraft 100 that is commonly referred to as a multicopter. Multicopter 100 may also be referred to as a quadcopter, as it includes four rotors 110. It should be understood that example embodiments may involve rotorcraft with more or less rotors than multicopter 100. For example, a helicopter typically has two rotors. Other examples with three or more rotors are possible as well. Herein, the term "multicopter" refers to any rotorcraft having more than two rotors, and the term "helicopter" refers to rotorcraft having two rotors.

Referring to multicopter 100 in greater detail, the four rotors 110 provide propulsion and maneuverability for the multicopter 100. More specifically, each rotor 110 includes blades that are attached to a motor 120. Configured as such the rotors may allow the multicopter 100 to take off and land vertically, to maneuver in any direction, and/or to hover. Furthermore, the pitch of the blades may be adjusted as a group and/or differentially, and may allow a multicopter 110 to perform three-dimensional aerial maneuvers such as an upside-down hover, a continuous tail-down "tic-toc," loops, loops with pirouettes, stall-turns with pirouette, knife-edge, immelmann, slapper, and traveling flips, among others. When the pitch of all blades is adjusted to perform such aerial maneuvering, this may be referred to as adjusting the "collective pitch" of the multicopter 100. Blade-pitch adjustment may be particularly useful for rotorcraft with substantial inertia in the rotors and/or drive train, but is not limited to such rotorcraft Additionally or alternatively, multicopter 100 may propel and maneuver itself by adjusting the rotation rate of the motors, collectively or differentially. This technique may be particularly useful for small electric rotorcraft with low inertia in the motors and/or rotor system, but is not limited to such rotorcraft.

Multicopter 100 also includes a central enclosure 130 with a hinged lid 135. The central enclosure may contain, e.g., control electronics such as an inertial measurement unit (IMU) and/or an electronic speed controller, batteries, other sensors, and/or a payload, among other possibilities.

The illustrative multicopter 100 also includes landing gear 140 to assist with controlled take-offs and landings. In other embodiments, multicopters and other types of UAVs without landing gear are also possible.

In a further aspect, multicopter 100 includes rotor protectors 150. Such rotor protectors 150 can serve multiple purposes, such as protecting the rotors 110 from damage if the multicopter 100 strays too close to an object, protecting the multicopter 100 structure from damage, and protecting nearby objects from being damaged by the rotors 110. It should be understood that in other embodiments, multicopters and other types of UAVs without rotor protectors are also possible. Further, rotor protectors of different shapes, sizes, and function are possible, without departing from the scope of the invention.

Figure 2:
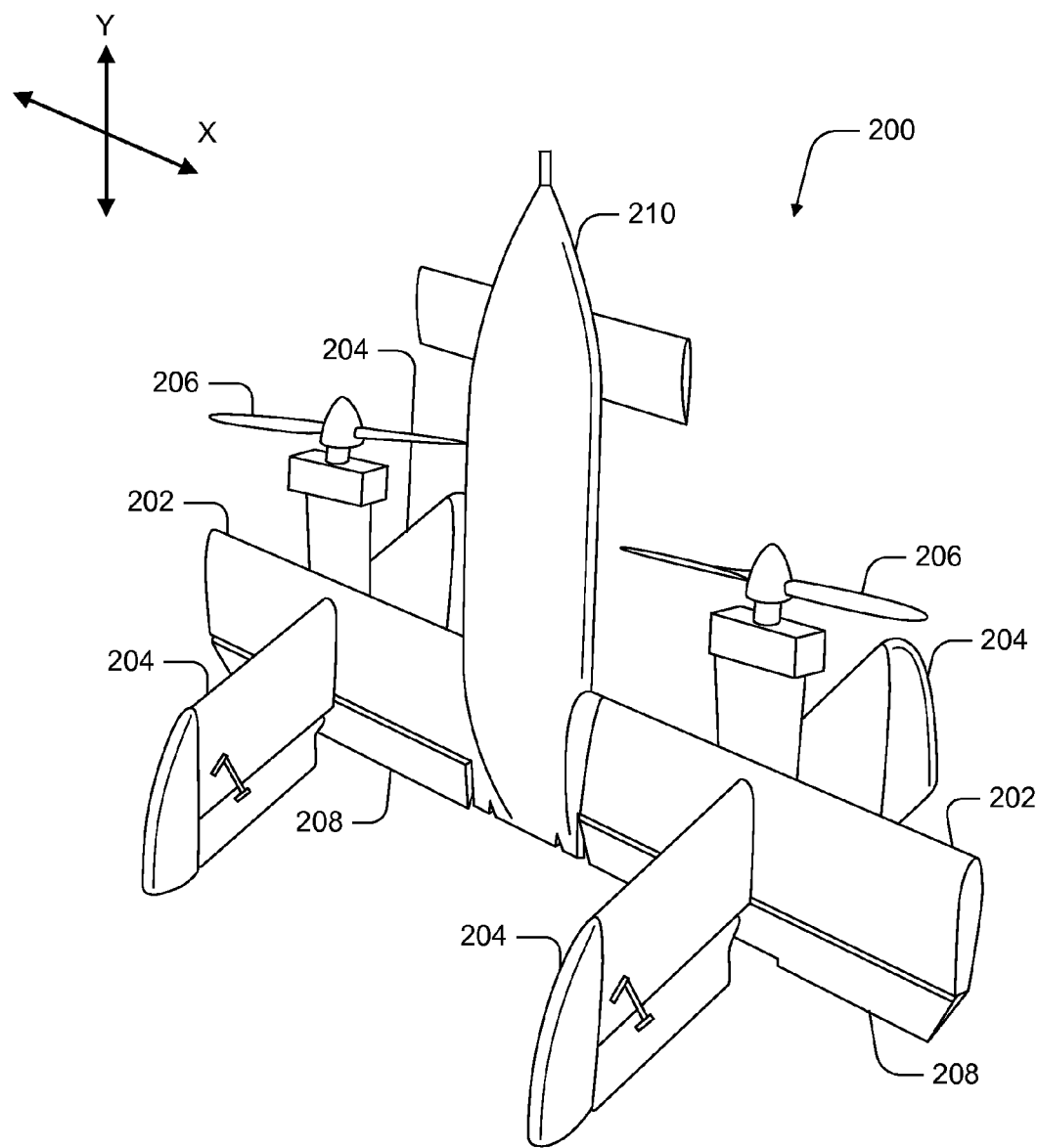

A multicopter 100 may control the direction and/or speed of its movement by controlling its pitch, roll, yaw, and/or altitude. To do so, multicopter 100 may increase or decrease the speeds at which the rotors 110 spin. For example, by maintaining a constant speed of three rotors 110 and decreasing the speed of a fourth rotor, the multicopter 100 can roll right, roll left, pitch forward, or pitch backward, depending upon which motor has its speed decreased. Specifically, the multicopter may roll in the direction of the motor with the decreased speed. As another example, increasing or decreasing the speed of all rotors 110 simultaneously can result in the multicopter 100 increasing or decreasing its altitude, respectively. As yet another example, increasing or decreasing the speed of rotors 110 that are turning in the same direction can result in the multicopter 100 performing a yaw-left or yaw-right movement. These are but a few examples of the different types of movement that can be accomplished by independently or collectively adjusting the RPM and/or the direction that rotors 110 are spinning FIG. 2 is a simplified illustration of a UAV, according to an example embodiment. In particular, FIG. 2 shows an example of a tail-sitter UAV 200. In the illustrated example, the tail-sitter UAV 200 has fixed wings 202 to provide lift and allow the UAV to glide horizontally (e.g., along the x-axis, in a position that is approximately perpendicular to the position shown in FIG. 2). However, the fixed wings 202 also allow the tail-sitter UAV 200 to take off and land vertically on its own.

For example, at a launch site, tail-sitter UAV 200 may be positioned vertically (as shown) with fins 204 and/or wings 202 resting on the ground and stabilizing the UAV in the vertical position. The tail-sitter UAV 200 may then take off by operating propellers 206 to generate the upward thrust (e.g., a thrust that is generally along the y-axis). Once at a suitable altitude, the tail-sitter UAV 200 may use its flaps 208 to reorient itself in a horizontal position, such that the fuselage 210 is closer to being aligned with the x-axis than the y-axis. Positioned horizontally, the propellers 206 may provide forward thrust so that the tail-sitter UAV 200 can fly in a similar manner as a typical airplane.

Variations on the illustrated tail-sitter UAV 200 are possible. For instance, tail-sitter UAVs with more or less propellers, or that utilize a ducted fan or multiple ducted fans, are also possible. Further, different wing configurations with more wings (e.g., an "x-wing" configuration with four wings), with less wings, or even with no wings, are also possible. More generally, it should be understood that other types of tail-sitter UAVs and variations on the illustrated tail-sitter UAV 200 are also possible.

As noted above, some embodiments may involve other types of UAVs, in addition or in the alternative to multicopters. For instance, FIGS. 3A and 3B are simplified illustrations of other types of UAVs, according to example embodiments.

Figure 3A:
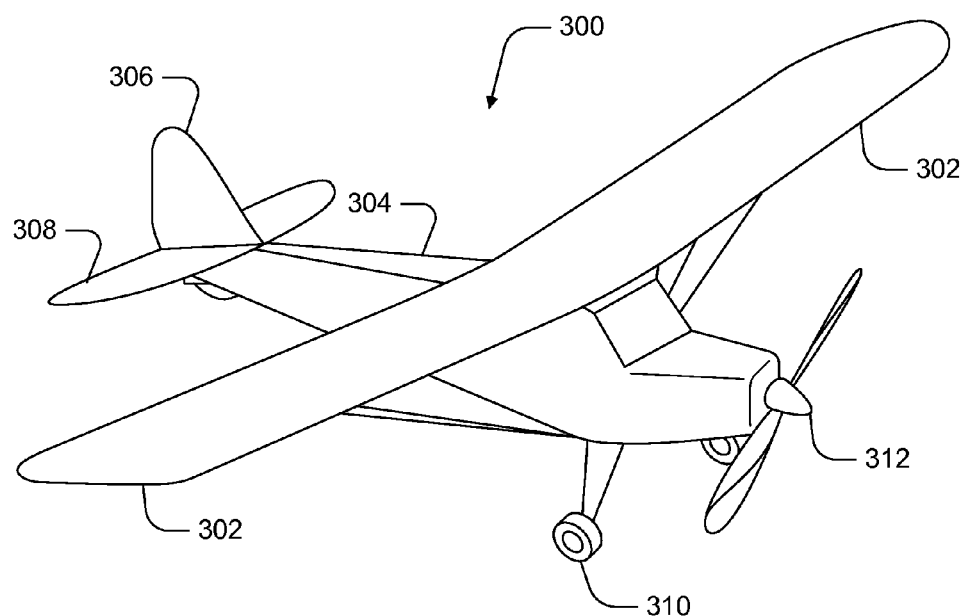

In particular, FIG. 3A shows an example of a fixed-wing aircraft 300, which may also be referred to as an airplane, an aeroplane, or simply a plane. A fixed-wing aircraft 300, as the name implies, has stationary wings 302 that generate lift based on the wing shape and the vehicle's forward airspeed. This wing configuration is different from a rotorcraft's configuration, which produces lift through rotating rotors about a fixed mast, and an ornithopter's configuration, which produces lift by flapping wings.

FIG. 3A depicts some common structures used in a fixed-wing aircraft 300. In particular, fixed-wing aircraft 300 includes a fuselage 304, two horizontal wings 302 with an airfoil-shaped cross section to produce an aerodynamic force, a vertical stabilizer 306 (or fin) to stabilize the plane's yaw (turn left or right), a horizontal stabilizer 308 (also referred to as an elevator or tailplane) to stabilize pitch (tilt up or down), landing gear 310, and a propulsion unit 312, which can include a motor, shaft, and propeller.

Figure 3B:
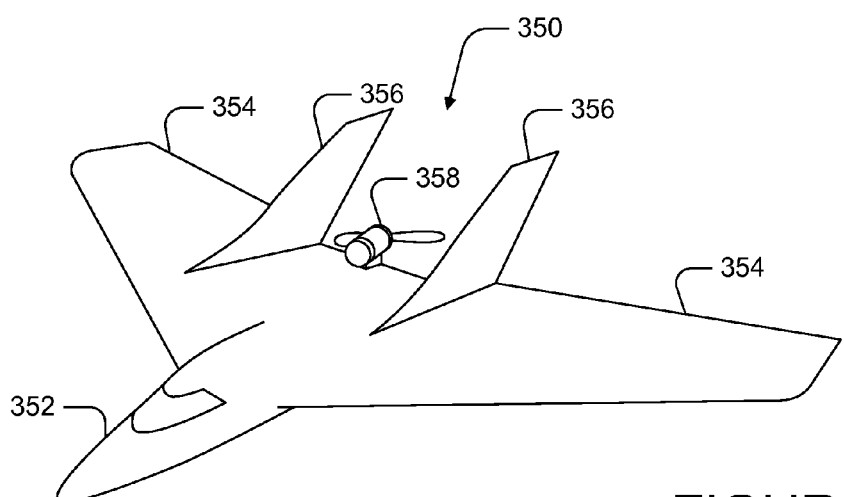

FIG. 3B shows an example of an aircraft 350 with a propeller in a pusher configuration. The term "pusher" refers to the fact that the propulsion unit 358 is mounted at the back of the aircraft and "pushes" the vehicle forward, in contrast to the propulsion unit being mounted at the front of the aircraft. Similar to the description provided for FIG. 3A, FIG. 3B depicts common structures used in the pusher plane: a fuselage 352, two horizontal wings 354, vertical stabilizers 356, and a propulsion unit 358, which can include a motor, shaft, and propeller.

UAVs can be launched in various ways, using various types of launch systems (which may also be referred to as deployment systems). A very simple way to launch a UAV is a hand launch. To perform a hand launch, a user holds a portion of the aircraft, preferably away from the spinning rotors, and throws the aircraft into the air while contemporaneously throttling the propulsion unit to generate lift.

Rather than using a hand launch procedure in which the person launching the vehicle is exposed to risk from the quickly spinning propellers, a stationary or mobile launch station can be utilized. For instance, a launch system can include supports, angled and inclined rails, and a backstop. The aircraft begins the launch system stationary on the angled and inclined rails and launches by sufficiently increasing the speed of the propeller to generate forward airspeed along the incline of the launch system. By the end of the angled and inclined rails, the aircraft can have sufficient airspeed to generate lift. As another example, a launch system may include a rail gun or cannon, either of which may launch a UAV by thrusting the UAV into flight. A launch system of this type may launch a UAV quickly and/or may launch a UAV far towards the UAV's destination. Other types of launch systems may also be utilized.

In some cases, there may be no separate launch system for a UAV, as a UAV may be configured to launch itself. For example, a "tail sitter" UAV typically has fixed wings to provide lift and allow the UAV to glide, but also is configured to take off and land vertically on its own. Other examples of self-launching UAVs are also possible.

In a further aspect, various other types of unmanned vehicles may be utilized to provide remote medical support. Such vehicles may include, for example, unmanned ground vehicles (UGVs), unmanned space vehicles (USVs), and/or unmanned underwater vehicles (UUVs). A UGV may be a vehicle which is capable of sensing its own environment and navigating surface-based terrain without input from a driver. Examples of UGVs include watercraft, cars, trucks, buggies, motorcycles, treaded vehicles, and retrieval duck decoys, among others. A UUV is a vehicle that is capable of sensing its own environment and navigating underwater on its own, such as a submersible vehicle. Other types of unmanned vehicles are possible as well.

III. Illustrative Medical-Support Systems with UAVs

As noted above, UAVs may be deployed to provide remote medical support. FIG. 4 is a simplified block diagram illustrating a medical-support system 400, according to an example embodiment.

In an illustrative medical-support system 400, an access system 402 may allow for interaction with, control of, and/or utilization of a network of medical-support UAVs 404. In some embodiments, an access system 402 may be a computing system that allows for human-controlled dispatch of UAVs 404. As such, the control system may include or otherwise provide a user interface (UI) 403 via which a user can access and/or control UAVs 404.

As a specific example, access system 402 could be a computing system at a police station or a fire station. Accordingly, a human operator at the police or fire station may receive an indication that a situation exists from a mobile or remote device 406 (e.g., a phone call, text message, etc.). The operator may then determine that medical support is appropriate and utilize access system 402 to dispatch one or more UAVs to provide the appropriate medical support. For example, the operator may use the UI 403 of access system 402 to request that a UAV be dispatched to the location of remote device 406 (or to another location indicated by the user of the remote device 406).

A UI 403 of an access system 402 may provide other functionality in addition to allowing for dispatch of UAVs 404. For example, UI 403 may allow an operator to specify certain details related to the medical situation to which the UAV is being dispatched. Examples of such details may include, but are not limited to: (a) general information related to the person or persons involved in the situation, such as age, height, weight, and so on, (b) medical information related to the person or persons involved in the situation, such as medical history, known allergies, and so on, (c) information related to the medical situation itself, such as symptoms exhibited by a person, details of events surrounding the situation (e.g., a car accident), and so on, and (d) desired specifications for the UAV to be dispatched, such as medical-support capabilities, wireless-communication capabilities, and so on.

Further, an access system 402 may provide for remote operation of a UAV. For instance, an access system 402 may allow an operator to control the flight of a UAV via UI 403. As a specific example, an operator may use an access system to dispatch a UAV 404 to the scene of a medical situation. The UAV 404 may then autonomously navigate to the general area where the medical situation is believed to exist (e.g., a stadium). At this point, the operator may use the access system 402 to take over control of the UAV 404, and navigate the UAV to the particular person in need of medical support (e.g., to the person's seat within the stadium). Other examples are also possible.

In an illustrative embodiment, UAVs 404 may take various forms. For example, each UAV 404 may be a UAV such as those illustrated in FIGS. 1, 2, 3A, and 3B. However, medical-support system 400 may also utilize other types of UAVs without departing from the scope of the invention. In some implementations, all UAVs 404 may be of the same or a similar configuration. However, in other implementations, UAVs 404 may include a number of different types of UAVs. For instance, UAVs 404 may include a number of types of UAVs, with each type of UAV being configured for a different type or types of medical support.

A remote device 406 may take various forms. Generally, a remote device 406 may be any device via which a request for medical support can be made and/or via which a situation that may require or benefit from medical support can be reported. For instance, a remote device 406 may be a mobile phone, tablet computer, laptop computer, personal computer, or any network-connected computing device. Further, in some instances, remote device 406 may not be a computing device. As an example, a standard telephone, which allows for communication via plain old telephone service (POTS), may serve as a remote device 406.

Further, a remote device 406 may be configured to communicate with access system 402 via one or more types of communication network(s) 414. For example, a remote device 406 could communicate with access system 402 (or via a human operator of the access system) by placing a phone call over a POTS network, a cellular network, and/or a data network such as the Internet. Other types of networks may also be utilized.

FIG. 4 also illustrates that the remote device 406 can be configured to communicate with the UAVs 404. For example, when the UAV 404 arrives within a nearby vicinity of the remote device 406, which is presumably at or near the location of the medical situation, the UAV can identify the remote device 406 and communicate therewith. Such communications can be short-range communications, for example, via radio frequency identification (RFID), wireless local-area networks (WLANs), and Bluetooth, although other short-range and long-range communication may also be utilized.

As noted above, a remote device 406 may be configured to allow a user to request medical support. For example, a person may use their mobile phone, a POTS phone, or a VoIP phone, to place an emergency call (e.g., a 9-1-1 call) and request that medical support be provided at the scene of an accident. Further, note that a request for medical support need not be explicit. For instance, a person may place a 9-1-1 call to report a medical situation. When the 9-1-1 operator receives such a call, the operator may evaluate the information that is provided and decide that medical support is appropriate. Accordingly, the operator may use an access system 402 to dispatch a UAV 404.

In a further aspect, a remote device 406 may be configured to determine and/or provide an indication of its own location. For example, remote device 406 may include a GPS system so that it can include GPS location information (e.g., GPS coordinates) in a communication to an access system 402 and/or to a dispatch system such as central dispatch system 408. As another example, a remote device 406 may use a technique that involves triangulation (e.g., between base stations in a cellular network) to determine its location. Alternatively, another system such as a cellular network may use a technique that involves triangulation to determine the location of a remote device 406, and then send a location message to the remote device 406 to inform the remote device of its location. Other location-determination techniques are also possible.

In an illustrative arrangement, central dispatch system 408 may be a server or group of servers, which is configured to receive dispatch messages requests and/or dispatch instructions from an access system 402. Such dispatch messages may request or instruct the central dispatch system 408 to coordinate the deployment of UAVs for remote medical support. A central dispatch system 408 may be further configured to route such requests or instructions to local dispatch systems 410. To provide such functionality, central dispatch system 408 may communicate with access system 402 via a data network, such as the Internet or a private network that is established for communications between access systems and automated dispatch systems.

In the illustrated arrangement, central dispatch system 408 may be configured to coordinate the dispatch of UAVs 404 from a number of different local dispatch systems 410. As such, central dispatch system 408 may keep track of which UAVs 404 are located at which local dispatch systems 410, which UAVs 404 are currently available for deployment, and/or which medical situation or situations each of the UAVs 404 is configured for. Additionally or alternatively, each local dispatch system 410 may be configured to track which of its associated UAVs 404 are currently available for deployment and/or which medical situation or situations each of its associated UAVs is configured for.

In some embodiments, when central dispatch system 408 receives a request for medical support from an access system 402, central dispatch system 408 may select a specific UAV 404 to dispatch. The central dispatch system 408 may accordingly instruct the local dispatch system 410 that is associated with the selected UAV to dispatch the selected UAV. The local dispatch system 410 may then operate its associated deployment system 412 to launch the selected UAV.

As a specific example, central dispatch system 408 may receive a request for medical support that indicates a certain type of medical situation and a location where the situation is occurring. Take, for instance, a request for medical support at the home of a person who appears to have suffered from cardiac arrest. In this scenario, the central dispatch system 408 may evaluate the fleet of UAVs 404 to select the closest available UAV to the person's home that is configured to provide medical support when a heart attack has occurred. Alternatively, the central dispatch system 408 may select an available UAV that is within a certain distance from the person's home (which may or may not be the closest), and which is configured to provide medical support when cardiac arrest has occurred.

In other embodiments, a central dispatch system 408 may forward a request for medical support to a local dispatch system 410 that is near the location where the support is requested, and leave the selection of a particular UAV 404 to the local dispatch system 410. For instance, in a variation on the above example, central dispatch system 408 may forward a request for medical support at the home of a person who appears to have suffered from a heart attack to the local dispatch system 410 that is closest to, or within a certain distance from, the person's home. Upon receipt of the request, the local dispatch system 410 may then determine which of its associated UAVs is configured to provide medical support to a heart-attack victim, and deploy this UAV.

In an example configuration, a local dispatch system 410 may be implemented in a computing system at the same location as the deployment system or systems 412 that it controls. For example, in some embodiments, a local dispatch system 410 could be implemented by a computing system at a building, such as a fire station, where the deployment systems 412 and UAVs 404 that are associated with the particular local dispatch system 410 are also located. In other embodiments, a local dispatch system 410 could be implemented at a location that is remote to its associated deployment systems 412 and UAVs 404.

Numerous variations on and alternatives to the illustrated configuration of medical-support system 400 are possible. For example, in some embodiments, a user of a remote device 406 could request medical support directly from a central dispatch system 408. To do so, an application may be implemented on a remote device 406 that allows the user to provide information regarding a medical situation, and generate and send a data message to request medical support. Such an application might also allow the user to request a particular type of medical support (e.g., by requesting that a UAV deliver a certain kind of medicine). In such an embodiment, central dispatch system 408 may include automated functionality to handle requests that are generated by such an application, evaluate such requests, and, if appropriate, coordinate with an appropriate local dispatch system 410 to deploy a UAV.

Further, in some implementations, some or all of the functionality that is attributed herein to central dispatch system 408, local dispatch system(s) 410, access system 402, and/or deployment system(s) 412 could be combined in a single system, implemented in a more complex system, and/or redistributed among central dispatch system 408, local dispatch system(s) 410, access system 402, and/or deployment system(s) 412 in various ways.

Yet further, while each local dispatch system 410 is shown as having two associated deployment systems, a given local dispatch system 410 may have more or less associated deployment systems. Similarly, while central dispatch system 408 is shown as being in communication with two local dispatch systems 410, a central dispatch system may be in communication with more or less local dispatch systems 410.

In a further aspect, a deployment system 412 may take various forms. In general, a deployment system may take the form of or include a system for physically launching a UAV 404. Further, a deployment system 412 may be configured to launch one particular UAV 404, or to launch multiple UAVs 404. A deployment system 412 may further be configured to provide additional functions, including for example, diagnostic-related functions such as verifying system functionality of the UAV, verifying functionality of devices that are housed within a UAV (e.g., such as a defibrillator, a mobile phone, or an HMD), and/or maintaining devices or other items that are housed in the UAV (e.g., by charging a defibrillator, mobile phone, or HMD, or by checking that medicine has not expired).

In some embodiments, the deployment systems 412 and their corresponding UAVs 404 (and possibly associated local dispatch systems 410) may be strategically distributed throughout an area such as a city. For example, deployment systems 412 may be located on the roofs of certain municipal buildings, such as fire stations, which can thus serve as the dispatch locations for UAVs 404. Fire stations may function well for UAV dispatch, as fire stations tend to be distributed well with respect to population density, their roofs tend to be flat, and the use of firehouse roofs as leased spaces for UAV dispatch could further the public good. However, deployment systems 412 (and possibly the local dispatch systems 410) may be distributed in other ways, depending upon the particular implementation.

In a further aspect, a medical-support system 400 may include or have access to a user-account database 414. The user-account database 414 may include data for a number of user-accounts, which are each associated with one or more person. For a given user-account, the user-account database 414 may include data related to the associated person or persons' medical history and/or may include other data related to the associated person or persons. Note that the medical-support system may only acquire, store, and utilize data related to a person with that person's explicit permission to do so.

Further, in some embodiments, a person may have to register for a user-account with the medical-support system 400 in order to use or be provided with medical support by the UAVs 404 of medical-support system 400. As such, the user-account database 414 may include authorization information for a given user-account (e.g., a user-name and password), and/or other information that may be used to authorize access to a user-account.

In some embodiments, a person may associate one or more of their devices with their user-account, such that they can be provided with access to the services of medical-support system 400. For example, when a person uses an associated mobile phone to, e.g., place a call to an operator of access system 402 or send a message requesting medical support to a dispatch system, the phone may be identified via a unique device identification number, and the call or message may then be attributed to the associated user-account. In addition or in the alternative to being an authorization mechanism, identifying the user-account may allow information such as the person's medical history to be used in responding to their request for medical support.

In a further aspect, the user-account database 414 may include data indicating a service level for each user. More specifically, a medical-support system 400 may provide service according to a number of different service levels, which correspond to different types of medical support. For example, a higher service level may: (a) provide access to additional types of UAVs, (b) provide medical support for additional medical situations, (c) provide access to improved support for a given medical situation, and/or (d) have priority as far as response time to requests for medical support, as compared to a lower service level. Other differences between a higher and lower service level are also possible.

In some embodiments, there may be no individual user accounts associated with a medical system; or, user accounts may exist but may not be used for purposes of determining whether a person should be provided medical support and/or for purposes of determining the quality of medical support that should be provided. For example, a medical support system may be implemented by a municipality or another public entity to provide medical support to citizens for free or at an equal cost. Other examples are also possible.

IV. Illustrative Components of a Medical-Support UAV

Figure 5:
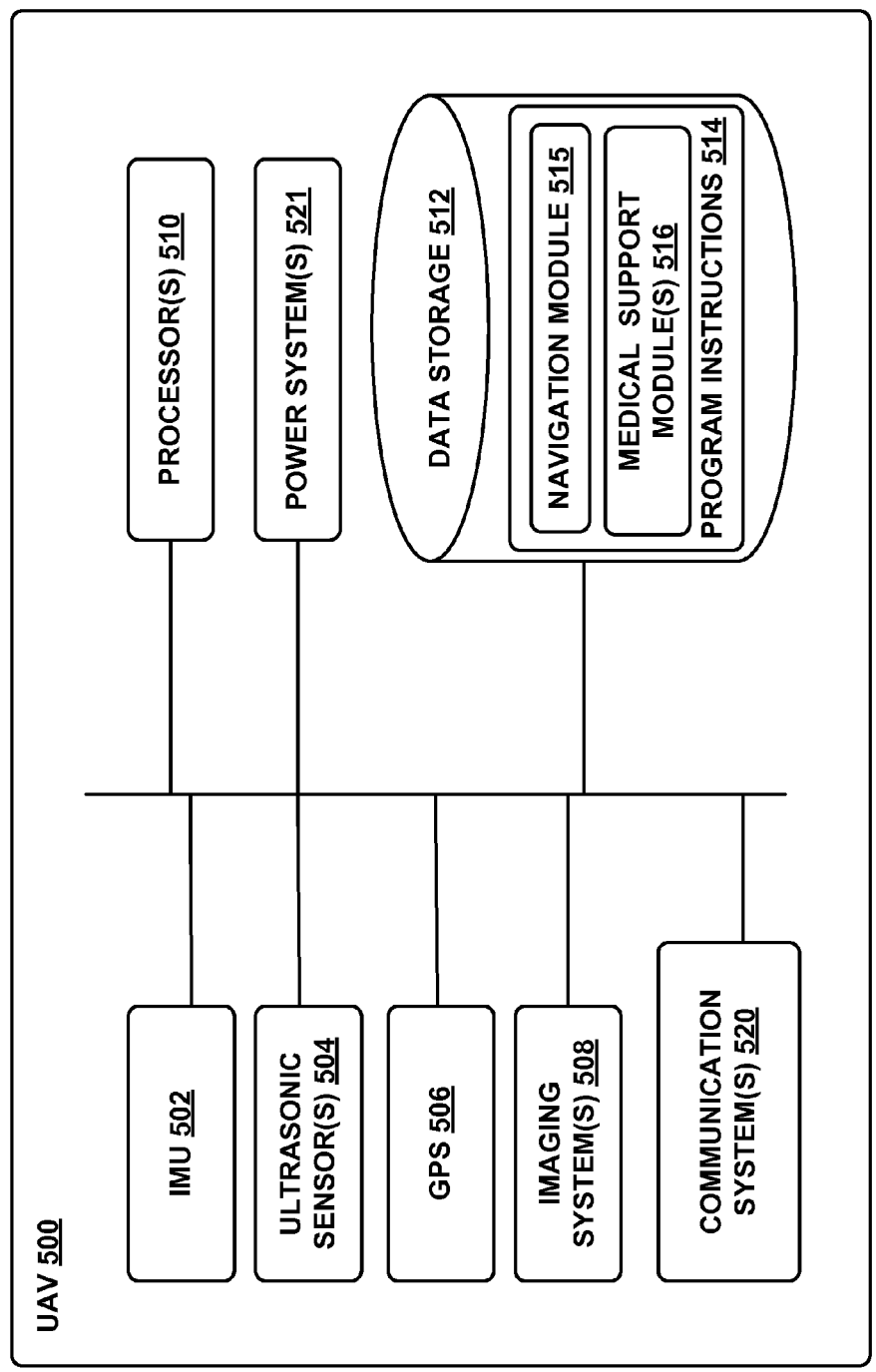
FIG. 5 is a simplified block diagram illustrating components of an unmanned aerial vehicle, according to an example embodiment.

FIG. 5 is a simplified block diagram illustrating components of a UAV 500, according to an example embodiment. UAV 500 may take the form of or be similar in form to one of the UAVs 100, 200, 300, and 350 shown in FIGS. 1, 2, 3A, and 3B. However, a UAV 500 may also take other forms.

UAV 500 may include various types of sensors, and may include a computing system configured to provide the functionality described herein. In the illustrated embodiment, the sensors of UAV 500 include an inertial measurement unit (IMU) 502, ultrasonic sensor(s) 504, GPS 506, imaging system(s) 508, among other possible sensors and sensing systems.

In the illustrated embodiment, UAV 500 also includes one or more processors 510. A processor 510 may be a general-purpose processor or a special purpose processor (e.g., digital signal processors, application specific integrated circuits, etc.). The one or more processors 510 can be configured to execute computer-readable program instructions 514 that are stored in the data storage 512 and are executable to provide the functionality of a UAV described herein.

The data storage 512 may include or take the form of one or more computer-readable storage media that can be read or accessed by at least one processor 510. The one or more computer-readable storage media can include volatile and/or non-volatile storage components, such as optical, magnetic, organic or other memory or disc storage, which can be integrated in whole or in part with at least one of the one or more processors 510. In some embodiments, the data storage 512 can be implemented using a single physical device (e.g., one optical, magnetic, organic or other memory or disc storage unit), while in other embodiments, the data storage 512 can be implemented using two or more physical devices.

As noted, the data storage 512 can include computer-readable program instructions 514 and perhaps additional data, such as diagnostic data of the UAV 500. As such, the data storage 514 may include program instructions to perform or facilitate some or all of the UAV functionality described herein. For instance, in the illustrated embodiment, program instructions 514 include a navigation module 515 and one or more medical-support modules 516.

A. Sensors

In an illustrative embodiment, IMU 502 may include both an accelerometer and a gyroscope, which may be used together to determine the orientation of the UAV 500. In particular, the accelerometer can measure the orientation of the vehicle with respect to earth, while the gyroscope measures the rate of rotation around an axis. IMUs are commercially available in low-cost, low-power packages. For instance, an IMU 502 may take the form of or include a miniaturized MicroElectroMechanical System (MEMS) or a NanoElectroMechanical System (NEMS). Other types of IMUs may also be utilized.

An IMU 502 may include other sensors, in addition to accelerometers and gyroscopes, which may help to better determine position and/or help to increase autonomy of the UAV 500. Two examples of such sensors are magnetometers and pressure sensors. Other examples are also possible. (Note that a UAV could also include such additional sensors as separate components from an IMU.)

While an accelerometer and gyroscope may be effective at determining the orientation of the UAV 500, slight errors in measurement may compound over time and result in a more significant error. However, an example UAV 500 may be able mitigate or reduce such errors by using a magnetometer to measure direction. One example of a magnetometer is a low-power, digital 3-axis magnetometer, which can be used to realize an orientation independent electronic compass for accurate heading information. However, other types of magnetometers may be utilized as well.

UAV 500 may also include a pressure sensor or barometer, which can be used to determine the altitude of the UAV 500. Alternatively, other sensors, such as sonic altimeters or radar altimeters, can be used to provide an indication of altitude, which may help to improve the accuracy of and/or prevent drift of an IMU.

In a further aspect, UAV 500 may include one or more sensors that allow the UAV to sense objects in the environment. For instance, in the illustrated embodiment, UAV 500 includes ultrasonic sensor(s) 504. Ultrasonic sensor(s) 504 can determine the distance to an object by generating sound waves and determining the time interval between transmission of the wave and receiving the corresponding echo off an object. A typical application of an ultrasonic sensor for unmanned vehicles or IMUs is low-level altitude control and obstacle avoidance. An ultrasonic sensor can also be used for vehicles that need to hover at a certain height or need to be capable of detecting obstacles. Other systems can be used to determine, sense the presence of, and/or determine the distance to nearby objects, such as a light detection and ranging (LIDAR) system, laser detection and ranging (LADAR) system, and/or an infrared or forward-looking infrared (FLIR) system, among other possibilities.

UAV 500 also includes a GPS receiver 506. The GPS receiver 506 may be configured to provide data that is typical of well-known GPS systems, such as the GPS coordinates of the UAV 500. Such GPS data may be utilized by the UAV 500 for various functions. For example, when a caller uses a mobile device to request medical support from a UAV, the mobile device may provide its GPS coordinates. As such, the UAV may use its GPS receiver 506 to help navigate to the caller's location, as indicated, at least in part, by the GPS coordinates provided by their mobile device. Other examples are also possible.

UAV 500 may also include one or more imaging system(s) 508. For example, one or more still and/or video cameras may be utilized by a UAV 500 to capture image data from the UAV's environment. As a specific example, charge-coupled device (CCD) cameras or complementary metal-oxide-semiconductor (CMOS) cameras can be used with unmanned vehicles. Such imaging sensor(s) 508 have numerous possible applications, such as obstacle avoidance, localization techniques, ground tracking for more accurate navigation (e.g., by applying optical flow techniques to images), video feedback, and/or image recognition and processing, among other possibilities.

In a further aspect, UAV 500 may use its one or more imaging system 508 to help in determining location. For example, UAV 500 may capture imagery of its environment and compare it to what it expects to see in its environment given current estimated position (e.g., its current GPS coordinates), and refine its estimate of its position based on this comparison.

In a further aspect, UAV 500 may include one or more microphones. Such microphones may be configured to capture sound from the UAVs environment.

B. Navigation and Location Determination

The navigation module 515 may provide functionality that allows the UAV 500 to, e.g., move about in its environment and reach a desired location. To do so, the navigation module 515 may control the altitude and/or direction of flight by controlling the mechanical features of the UAV that affect flight (e.g., rotors 110 of UAV 100).

In order to navigate the UAV 500 to a target location, a navigation module 515 may implement various navigation techniques, such as map-based navigation and localization-based navigation, for instance. With map-based navigation, the UAV 500 may be provided with a map of its environment, which may then be used to navigate to a particular location on the map. With localization-based navigation, the UAV 500 may be capable of navigating in an unknown environment using localization. Localization-based navigation may involve a UAV 500 building its own map of its environment and calculating its position within the map and/or the position of objects in the environment. For example, as a UAV 500 moves throughout its environment, the UAV 500 may continuously use localization to update its map of the environment. This continuous mapping process may be referred to as simultaneous localization and mapping (SLAM). Other navigation techniques may also be utilized.

In some embodiments, the navigation module 515 may navigate using a technique that relies on waypoints. In particular, waypoints are sets of coordinates that identify points in physical space. For instance, an air-navigation waypoint may be defined by a certain latitude, longitude, and altitude. Accordingly, navigation module 515 may cause UAV 500 to move from waypoint to waypoint, in order to ultimately travel to a final destination (e.g., a final waypoint in a sequence of waypoints).

In a further aspect, navigation module 515 and/or other components and systems of UAV 500 may be configured for "localization" to more precisely navigate to the scene of a medical situation. More specifically, it may be desirable in certain situations for a UAV to be close to the person in need of medical support (e.g., within reach of the person), so as to properly provide medical support to the person. To this end, a UAV may use a two-tiered approach in which it uses a more-general location-determination technique to navigate to a target location or area that is associated with the medical situation, and then use a more-refined location-determination technique to identify and/or navigate to the target location within the general area.

For example, a UAV 500 may navigate to the general area of a person in need using waypoints that are pre-determined based on GPS coordinates provided by a remote device at the scene of the medical situation. The UAV may then switch to a mode in which it utilizes a localization process to locate and travel to a specific location of the person in need. For example, if a person is having a heart attack at a large stadium, a UAV 500 carrying a medical package may need to be within reach of the person or someone near the person so that the can take items from the package. However, a GPS signal may only get a UAV so far, e.g., to the stadium. A more precise location-determination technique may then be used to find the specific location of the person within the stadium.

Various types of location-determination techniques may be used to accomplish localization of a person once a UAV 500 has navigated to the general area of the person. For instance, a UAV 500 may be equipped with one or more sensory systems, such as, for example, imaging system(s) 508, a directional microphone array (not shown), ultrasonic sensors 504, infrared sensors (not shown), and/or other sensors, which may provide input that the navigation module 515 utilizes to navigate autonomously or semi-autonomously to the specific location of a person.

As another example, once the UAV 500 reaches the general area of the person, the UAV 500 may switch to a "fly-by-wire" mode where it is controlled, at least in part, by a remote operator, who can navigate the UAV 500 to the specific location of the person in need. To this end, sensory data from the UAV 500 may be sent to the remote operator to assist them in navigating the UAV to the specific location. For example, the UAV 500 may stream a video feed or a sequence of still images from the UAV's imaging system(s) 508. Other examples are possible.

As yet another example, the UAV 500 may include a module that is able to signal to a passer-by for assistance in either reaching the specific location or delivering its medical-support items to the medical situation; for example, by displaying a visual message in a graphic display, playing an audio message or tone through speakers, flashing a light, or performing a combination of such functions. Such visual or audio message might indicate that assistance is needed in delivering the UAV 500 to the person in need, and might provide information to assist the passer-by in delivering the UAV 500 to the person, such a description of the person, the person's name, and/or a description of the person's specific location, among other possibilities. This implementation can be useful in a scenario in which the UAV is unable to use sensory functions or another location-determination technique to determine the specific location of the person.

As an additional example, once a UAV 500 arrives at the general area of a person, the UAV may utilize a beacon from the remote device (e.g., the mobile phone of a person who called for medical support) to locate the person. Such a beacon may take various forms. As an example, consider the scenario where a remote device, such as the mobile phone of a person in need or a bystander, is able to send out directional signals (e.g., an RF signal, a light signal, and/or an audio signal). In this scenario, the UAV may be configured to navigate by "sourcing" such directional signals—in other words, by determining where the signal is strongest and navigating accordingly. As another example, a mobile device can emit a frequency, either in the human range or outside the human range, and the UAV can listen for that frequency and navigate accordingly. As a related example, if the UAV is listening for spoken commands, then the UAV could utilize spoken statements, such as "Help! I'm over here!" to source the specific location of the person in need of medical assistance.

In an alternative arrangement, a navigation module may be implemented at a remote computing device, which communicates wirelessly with the UAV. The remote computing device may receive data indicating the operational state of the UAV, sensor data from the UAV that allows it to assess the environmental conditions being experienced by the UAV, and/or location information for the UAV. Provided with such information, the remote computing device may determine altitudinal and/or directional adjustments that should be made by the UAV and/or may determine how the UAV should adjust its mechanical features (e.g., rotors 110 of UAV 100) in order to effectuate such movements. The remote computing system may then communicate such adjustments to the UAV so it can move in the determined manner.

C. Communication Systems

In a further aspect, UAV 500 includes one or more communication systems 520. The communications systems 520 may include one or more wireless interfaces and/or one or more wireline interfaces, which allow UAV 500 to communicate via one or more networks. Such wireless interfaces may provide for communication under one or more wireless communication protocols, such as Bluetooth, WiFi (e.g., an IEEE 802.11 protocol), Long-Term Evolution (LTE), WiMAX (e.g., an IEEE 802.16 standard), a radio-frequency ID (RFID) protocol, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network.

In an example embodiment, a UAV 500 may include communication systems 520 that allow for both short-range communication and long-range communication. For example, the UAV 500 may be configured for short-range communications with a range of about 50 meters or less using WiFi, RFID, NFC, ZigBee, short-range infrared (IR) communication, and Bluetooth. The UAV 500 may also be configured for long-range communications under a CDMA protocol, an LTE protocol, or WiMAX, for example. In such an embodiment, the UAV 500 may be configured to function as a "hot spot" or in other words, as a gateway or proxy between a remote support device and one or more data networks, such as cellular network and/or the Internet. Configured as such, the UAV 500 may facilitate data communications that the remote support device would otherwise be unable to perform by itself.

For example, UAV 500 may provide a WiFi connection to a remote device, and serve as a proxy or gateway to a cellular service provider's data network, which the UAV might connect to under an LTE or a 3G protocol, for instance. The UAV 500 could also serve as a proxy or gateway to a high-altitude balloon network, a satellite network, or a combination of these networks, among others, which a remote device might not be able to otherwise access.

D. Power Systems

In a further aspect, UAV 500 may include power system(s) 521. A power system 521 may include one or more batteries for providing power to the UAV 500. In one example, the one or more batteries may be rechargeable and each battery may be recharged via a wired connection between the battery and a power supply and/or via a wireless charging system, such as an inductive charging system that applies an external time-varying magnetic field to an internal battery.

E. Medical-Support Functionality

As noted above, UAV 500 may include one or more medical-support modules 516. The one or more medical-support modules 516 include software, firmware, and/or hardware that may help to provide or assist in the provision of the medical-support functionality described herein. Further, the medical-support modules 516 can be configured to be enabled or authorized to provide or assist in the provision of the medical-support functionality in response to a determination that the UAV 500 is in a nearby vicinity (e.g., within about 50 meters) of a remote device, such as the remote device 406 of FIG. 4.

Configured as such, a UAV 500 may provide medical support in various ways. For instance, a UAV 500 may have stored information that can be provided to a person or persons at the target location, in order to assist the person or persons in providing medical care. For example, a UAV may include a video or audio file with instructions for providing medical support, which the UAV can play out to a person at the target location. As another example, a UAV may include an interactive program to assist a person at the target location in providing medical support. For instance, a UAV may include an application that analyzes the person's speech to detect questions related to the medical situation and/or that provides a text-based interface via which the person can ask such questions, and then determines and provides answers to such questions.

In some embodiments, a UAV 500 may facilitate communication between a layperson and/or medical personnel at the scene and medical personnel at a remote location. As an example, a medical-support module 516 may provide a user interface via which a person at the scene can use a communication system 520 of the UAV to communicate with an emergency medical technician at a remote location. As another example, the UAV 500 can unlock certain capabilities of a remote device, such as a mobile phone, which is near the UAV at the scene of an medical situation. Such capabilities may be inaccessible to a user of the remote device, unless the remote device is within a certain distance from the UAV such that the UAV can unlock the capabilities. For example, a UAV may send the remote device a security key that allows the remote device to establish a secure connection to communicate with medical personnel at a remote location. Other examples are also possible.

Further, in order to provide medical support at a remote location, a UAV 500 may be configured to transport items to the scene of a medical situation. Such items may aid in diagnosing and/or treating a person who needs medical assistance, or may serve other purposes. Such items may include, as examples: (a) medicines, (b) diagnostic devices, such as a pulse oximeter, blood pressure sensor, or EKG sensor, (c) treatment devices, such as an EpiPen, a first aid kit, or various kinds of defibrillators (e.g., an automated external defibrillator (AED)), and/or (d) remote support devices, such as a mobile phone or a head-mountable device (HMD), among other possibilities. Note that some items that are electronic may include one or more batteries to provide power to the item. These batteries may be rechargeable and may be recharged using one or more wired or wireless charging systems. In addition or in the alternative, an item may be integrated with one or more batteries in the power system 521 for power.

A UAV 500 may employ various systems and configurations in order to transport items to the scene of a medical situation. For example, as shown in FIG. 1, a UAV 100 can include a compartment 135, in which an item or items may be transported. As another example, the UAV can include a pick-and-place mechanism, which can pick up and hold the item while the UAV is in flight, and then release the item during or after the UAV's descent. As yet another example, a UAV could include an air-bag drop system, a parachute drop system, and/or a winch system that is operable from high above a medical situation to drop or lower an item or items to the scene of the medical situation. Other examples are also possible.

In some implementations, a given UAV 500 may include a "package" designed for a particular medical situation (or possibly for a particular set of medical situations). A package may include one or more items for medical support in the particular medical situation, and/or one or more medical-support modules 516 that are designed to provide medical support in the particular medical situation. In some cases, a UAV 500 may include a package that is designed for a particular medical situation such as choking, cardiac arrest, shock, asthma, drowning, etc.

In other cases, a UAV 500 may include a package that is designed for a number of different medical situations, which may be associated in some way. For example, a dive-accident package may be designed to provide or assist in provision of care in various medical situations that are often associated with a scuba diving accident, such as drowning and/or decompression sickness. Such a dive-accident package might include a flotation device, an oxygen-therapy system, a system for delivering visual and/or audible medical care instructions (e.g., instructions for performing CPR), and/or a signaling device, among other possibilities. A UAV 500 that is configured with such a dive-accident package may be referred to herein as a "dive-rescue" UAV. Such a dive-rescue UAV may be deployed to a diver on the surface of the water, who has just had an accident while scuba diving, with the hope that the UAV can reach the diver and deliver medical treatment sooner than would otherwise be possible.

For instance, provided with the above dive-accident package, the UAV 500 may drop a flotation device to help the diver stay afloat until the diver can be reached by rescuers. In addition, the UAV may include a signaling device, which can be automatically turned on when the UAV locates the diver. Doing so may help a rescue boat locate a diver more quickly. Further, once the diver has been rescued, the UAV may display visual instructions and/or play back auditory instructions for CPR, which may help to revive a drowning victim. Such instructions may be particularly useful in the case where the diver is rescued by non-medical professionals; if the diver is rescued by a passing fishing boat, for example.

Further, when the UAV arrives at the scene of a dive accident or, more likely, once the diver has been moved to a rescue boat, the UAV could provide an oxygen-therapy system, and possibly instructions for use thereof, in order to treat possible decompression sickness. Since a rescue boat might not have oxygen-therapy system, and immediate administration of pure oxygen has been shown to increase the probability of recovering from decompression sickness, such functionality of a UAV could improve treatment for a diver suffering from decompression sickness.

In some embodiments, a UAV 500 could include an integrated system or device for administering or assisting in the administration of medical care (e.g., a system or device having one or more components that are built in to the structure of the UAV itself). For example, as noted above, a UAV could include an oxygen-therapy system. In an example configuration, an oxygen-therapy system might include a mask that is connected via tubing to an on-board oxygen source. Configured as such, the UAV could release the oxygen mask when it reaches a person in need of oxygen (e.g., at a fire scene).

As another example of a UAV with an integrated medical-support device, a UAV 500 might function as a mobile defibrillator. Specifically, rather than carry a stand-alone defibrillator that can then be removed from the UAV for use, the UAV itself may function as a defibrillator.

As a specific example, a multicopter might include components of an AED that is built into its body, as well as retractable electrode pads for administering a shock to a person who is experiencing a cardiac event or arrest. When the multicopter arrives at the scene of cardiac arrest, the multicopter may land, disable its rotors, and enter a mode where it functions as an AED. Specifically, after landing, the multicopter may release its retractable electrode pads and provide instructions so that a bystander, who might be layperson, could use the electrode pads to administer care to the person with a cardiac arrest. Such instructions may be provided, for example, by displaying text and/or video on a graphic display that is built in to the body of the multicopter, and/or by playing back audio instructions. The multicopter could also include a wireless communication interface via which a bystander could communicate with a live remote operator (e.g., a medical professional at a remote location), in order to receive instructions for using the AED.

Many other examples and variations on the above examples of UAVs with integrated medical-support systems and devices are also possible. For instance, a medical device may be integrated into the structure of a UAV itself when doing so reduces weight, improves aerodynamics, and/or simplifies the use of the device by a person at the scene of the medical situation. Further, those skilled in the art will appreciate that a medical-support system or device may be integrated in the structure of a UAV in other situations and for other reasons.

In some applications, a UAV 500 may be dispatched to the scene of a medical situation to provide early intelligence to medical personnel. In particular, a UAV 500 may be dispatched because it is expected to reach the location of a medical situation more rapidly than medical personnel are able to. In this scenario, the UAV 500 may arrive at the scene and provide early intelligence by communicating information and providing situational awareness to medical personnel. For example, a UAV 500 may use its imaging system(s) 508 to capture video and/or still images at the scene of the medical situation, which the UAV 500 may communicate to medical and/or emergency personnel. As another example, UAV 500 could administer preliminary tests to a person in need, or request that a bystander administer certain preliminary diagnostic tests and/or provide certain information. UAV 500 may then send such test results and/or such information provided by a bystander to medical and/or emergency personnel. A UAV 500 may provide other types of early-intelligence information as well.

By providing early intelligence to medical and/or emergency personnel, a UAV 500 may help the medical and/or emergency personnel to prepare to provide care, such that more effective care can be provided once the personnel arrive at the scene. For instance, a UAV 500 could send video, test results, and/or bystander-provided information to medical personnel while they are travelling in an ambulance on their way to the scene, to firemen or other personnel while they are in a fire truck on their way to the scene, and/or to police they are in a law-enforcement vehicle on their way to the scene, among other possibilities.

It should be understood that the examples of medical-support functionality that are provided herein are not intended to be limited. A UAV may be configured to provide other types of medical-support functionality without departing from the scope of the invention.

V. Illustrative Methods

FIG. 6 is a flow chart illustrating a method 600, according to an example embodiment. Illustrative methods, such as method 600, may be carried out in whole or in part by a component or components in a medical-support system, such as by the one or more of the components of the medical-support system 400 shown in FIG. 4. For simplicity, method 600 may be described generally as being carried out by a medical-support system, such as by one or more of a UAV 400, an access system 402, a remote device 406, a central dispatch system 408, a local dispatch system 410, and/or a deployment system 412. However, it should be understood that example methods, such as method 600, may be carried out by other entities or combinations of entities (e.g., by other computing devices and/or combinations of computing devices), without departing from the scope of the invention.

As shown by block 602, method 600 involves a medical-support system identifying a remote medical situation. The medical-support system may also determine the target location corresponding to the medical situation, as shown by block 604. The medical-support system can then select a UAV from a plurality of UAVs, where the selection of the UAV is based at least in part on a determination that the selected UAV is configured for the identified medical situation, as shown by 606. More specifically, in an illustrative embodiment, the medical-support system may have a number of UAVs available for dispatch, which are configured for a number of different medical situations (with some or all of the UAVs being configured differently from one another). Accordingly, at block 606, the medical-support system may select the particular UAV that is appropriate for the identified medical situation. The medical-support system may then cause the selected UAV to travel to the target location to provide medical support, as shown by block 608.

FIG. 7 is a flow chart illustrating another method 700, according to an example embodiment. The method 700 may be carried out in whole or in part by a component or components in a medical-support system, such as by the one or more of the components of the medical-support system 400 shown in FIG. 4. For simplicity, method 700 may be described generally as being carried out by a medical-support system, such as by one or more of a UAV 400 and a remote device 406. However, it should be understood that the method 700 may be carried out by other entities or combinations of entities (e.g., by other computing devices and/or combinations of computing devices), without departing from the scope of the invention.

As described above with respect to FIG. 6, a medical-support system can identify a remote medical situation and cause a selected UAV to travel to a target location to provide medical support. Referring to FIG. 7, as shown by block 702, method 700 involves a UAV traveling to a nearby vicinity (e.g., within about 50 meters) of a target location of the medical situation. Once the UAV arrives at the vicinity of the target location, at block 704, the UAV communicates with the remote device to determine that the UAV is within the nearby vicinity of the remote device. Thereafter, at block 706, the UAV and/or the remote device enable or authorize a capability that can be utilized to assist in the medical situation. At block 706, the remote device may first prompt a user to grant permission before the capability is enabled or authorized.

A. Identifying a Remote Medical Situation

Referring again to the method 600 of FIG. 6, various types of medical situations may be identified at block 602 of method 600. For example, a medical-support system could identify a medical situation, such as the occurrence of a heart attack, a stroke, an anaphylactic shock, a broken bone, heat stroke, or any of a large number of other medical situations. More generally, a medical situation may be any situation where a person or possibly even an animal (e.g., a pet dog or cat) might benefit from medical support or treatment. In another example, the medical-support system could identify a hazardous situation emergency, such as a fire or chemical spill, a building collapse, a rescue situation, and the like. In yet another example, the medical-support system could identify a law enforcement emergency such as a rescue situation among other examples. Generally, the medical-support system can identify any type of emergency situation that could be associated with a 9-1-1 call or some other central emergency response system.

In some embodiments, however, a medical-support system may place more stringent requirements on what is classified as a medical situation to which a UAV should be dispatched. In particular, since deploying and operating an UAV may be costly, a medical-support system may only dispatch a UAV in a situation where the UAV is expected to provide more immediate and/or superior medical support, as compared to traditional medical response services. In some embodiments, the medical-support system may even engage in cost-benefit analysis to determine whether the expected benefit of sending a UAV outweighs the expense of doing so. Other criteria for determining what is and is not considered a medical situation that justifies use of a UAV are also possible, and may vary depending upon the particular implementation.

In other embodiments, the benefit of having a UAV there slightly earlier may be great enough that the UAV may be deployed as soon as a possible medical situation is reported; without waiting to determine whether the use of a UAV is justified. Then, at a later time (e.g., 30-60 seconds after launch), the medical-support system may have a better understanding as to whether or not the possible medical situation is in fact a medical situation to which a UAV should be deployed. If it is not, then the UAV may recalled; or the UAV may automatically return if it does not receive a message indicating that it should continue to the location of the medical situation.

At block 602, the identification of the remote medical situation may involve a component of the medical-support system receiving a communication that originated from a remote device, and identifying the remote medical situation based on information provided by the communication. Generally, the communication may include a request for assistance in a remote medical situation. Such a communication may take various forms, such as a phone call, a text-message, or an electronic message generated by an application of a remote device, as just a few examples. In some embodiments, an automated computer program on a remote device may act as a notifier and initiate a communication to report a medical situation. For example, a body-monitoring device may detect a possible medical situation, such as a stroke or heart attack, and automatically notify a medical-support system. Other examples are also possible.

At block 602, the identification of a request for assistance in a medical situation can be received from a remote device associated with the medical situation. For example, a remote device that made the request for assistance or remote device identified as a point-of-contact for the medical situation. In another example, at block 602, the medical-support system can also identify the remote device associated with the medical situation.

In some embodiments, the communication may include location information, such as GPS coordinates of the remote device. Such location information may be utilized at block 604 to determine the location of the remote device, which may in turn be assumed to be or otherwise used to determine the location of the medical situation.

Further, in order to identify what the particular medical situation is, the medical-support system may utilize information provided via the communication from the remote device. Specifically, such information may be used in an effort to better identify the type of medical situation that is at issue, or to identify a class of medical situations for which the person's medical situation likely qualifies. In some embodiments, this information may be provided by the person operating the remote device, who may be referred to herein as the "notifier." For instance, a notifier might provide information such as the observed symptoms of a person in need (e.g., "my friend just collapsed and is convulsing" or "I am having chest pains"). In some instances, the notifier might purport to convey the type of medical itself ("my brother is having a stroke!"). Further, a notifier might provide location information and/or other types of information related to an medical situation.

In another example, the notifier might provide communication connectivity information of a remote device that is used to make the request for medical support (e.g., "my friend just fell and was injured while hiking at the Grand Canyon; I had to get to higher ground to receive cell phone service and request medical support).

The information provided via the communication from the remote device may take various forms. For example, the notifier may provide information via a voice call, in which case they can simply speak with a live operator (e.g., a live operator at access system 402). Alternatively, a speech-to-text module could be implemented by the medical-support system to convert the speech from a phone call to text, which can then be analyzed to derive the information about the medical situation. Information related to a medical situation may also be provided via text, such as via a text message or a message that is generated via an application on the remote device.

In some embodiments, the medical-support system may obtain information from image data that is captured at the scene of a medical situation, which may then be used to determine what the particular medical situation is. Such image data may be captured by and/or sent from a remote device at the scene of the medical situation. In particular, a notifier may use the camera of their mobile phone to capture and send video and/or still images to the medical-support system, possibly in real-time. As examples, a bystander may capture an image or video of an injured limb, or possibly even video of an accident taking place, and such image data to the medical-support system. Other examples are possible.

In some embodiments, the information provided by the notifier may include other types of data. For example, a remote device may include an application for reporting a medical situation and/or requesting medical support. Such an application may provide a UI with features that allow a user of the remote device to quickly provide information relating to a medical situation. For instance, a user could hit a button to indicate what type of medical situation they believe to be occurring, select checkboxes from a symptoms checklist to indicate observed symptoms, and so on. Further, such an application may allow the user to initiate a communication to relay data indicating the provided information to a medical-support system. Other examples are also possible.

In some embodiments, the information provided by the notifier can be used in combination with other information that is known or accessible to the medical-support system. As an example, consider a scenario where a notifier, who is at the beach on a 100-degree day, calls the medical-support system from their mobile phone and says, "someone here just collapsed!" The medical-support system may then determine the location of the mobile phone, use enhanced mapping data to determine that the mobile phone's location is at a beach, and look up the current temperature at the determined location. Then, using the notifier's spoken information, together with the local temperature and the fact that location information corresponds to a beach, the medical-support system may deduce that the medical situation is likely to be heat exhaustion or a related condition.

In the embodiments described above, block 602 involves the medical-support system using various types of information to actively determining what the particular medical situation is likely to be. As another example, and referring to FIG. 4, when a remote device 406 contacts an operator at an access system 402 to report a medical situation, the access system may automatically extract and analyze information from the communication to identify what the medical situation is, or determine a list of possible medical situations based on the available information. The access system 402 may then display an indication of the identified medical situation or the list of possible medical situations, so that the operator can confirm or select the medical situation they believe is occurring and, if appropriate, instruct the dispatch system (e.g., central dispatch system 408) to send a UAV. Alternatively, when the access system positively identifies a particular medical situation, the access system may automatically instruct the dispatch system to dispatch a UAV, without requesting authorization from an operator.

Note that in some cases, the identification of the remote medical situation could simply involve the medical-support system receiving a communication that indicates what the medical situation is. In other words, the medical-support system may identify the medical situation by passively being told what it is by a remote device or by a human operator of the medical-support system (e.g., a live operator at access system 402), for example.

B. Determining the Target Location

As noted above, block 604 of method 600 involves a medical-support system determining a target location that corresponds to the identified medical situation. For example, when a medical-response service is notified of a medical situation, the service will likely need to determine the general location of the person in need, so that a UAV can be deployed to assist the person.

In some embodiments, the target location may be the location of the person or persons who are likely to benefit from medical support in the given medical situation (or an estimate of such person or persons' location or locations). For example, if a person who is in need of medical care places an emergency call from their own mobile phone, the target location may be determined to be (or otherwise based on) the location of their mobile phone. As another example, if a bystander places an emergency call from their mobile phone in order to report a medical situation that involves another person, it may be assumed or otherwise determined that the bystander is at or near the location of the other person. Accordingly, the target location may be set to (or otherwise determined from) the location of the bystander's mobile phone.

In other embodiments, the target location may be different from the location of the person or persons who are likely to benefit from medical support. For example, consider a scenario where an emergency medical technician (EMT) or paramedic is closer to the location of a person in need of medical support, but the EMT or paramedic does not have certain medical supplies that are needed for or might improve the medical care that can be provided. In this scenario, a medical-support system may dispatch a UAV to the location of the EMT or paramedic in order to deliver medical supplies to the EMT or paramedic, so that they can take them with them to the scene of the medical situation. Further, in some cases, the UAV might even be configured to deliver the medical supplies to the EMT or paramedic as they travel to the scene of the medical situation. In such case, the target location (e.g., the location of the EMT or paramedic) may be dynamically updated to reflect the movement of the EMT or paramedic as they travel to the scene.

The target location may be determined in a number of ways, and may be based on various types of location information. For instance, in some embodiments, the target location may be determined based on information that is provided by the remote device from which the indication of the medical situation was received. For example, consider a scenario where a bystander calls "911" and says "Somebody near me just collapsed!" Typically, when receiving a phone call, the police also receive location information, such as GPS coordinates, which identify the location of the remote device. This location information may then be made available to a medical-support system or otherwise accessible for purposes of determining the target location. For example, when a remote device calls to report a medical situation, an operator at an access system or an automated dispatch system could determine the location of the remote device based on such received GPS coordinates.

A medical-support system may determine and/or be provided with information that can be used to determine the target location in other ways. For instance, in some embodiments, part or all of the process of determining the target location could be automated or, in other words, performed without a need for human intervention. To this end, the emergency-support system could utilize any suitable information-recognition technique, such as, for example, voice recognition (when the notification is spoken) or character recognition (when the notification is typed), among other techniques now known or later developed. As an example, consider a scenario where a bystander calls 911 and says: "Somebody near me just collapsed! I'm at 123 Main Street, Mountain View." In this situation, an automated dispatch system could apply speech-to-text processing to analyze the bystander's words and determine the stated address therefrom.

The above techniques for determining such target locations are provided for illustrative purposes and not intended to be limiting. It should be understood that other techniques may be used to determine a target location, to which a UAV may be dispatched by an medical-support system.

C. Selecting an Unmanned Aerial Vehicle

As noted above, at block 606 of method 600, a medical-support system may select a UAV that is configured to provide medical support for the particular medical situation. In particular, a medical-support system may include or have access to a number of different types of UAVs, which are configured to provide medical support in various different medical scenarios. As such, different UAVs may be said to have a different "medical-support configurations." Thus, block 606 may involve a medical-support system selecting a UAV that has a medical-support configuration that is likely to provide or assist in providing medical support for the particular medical situation.

In some cases, the medical-support configuration of a given type of UAV may include a package of one or more items that are designed to provide or assist in providing medical support for a certain medical situation. For example, a given type of UAV could include Aspirin and a defibrillator, and thus might be selected as an appropriate UAV to deploy when the medical-support system receives an indication that a heart attack or cardiac arrest is occurring or has just occurred. Many other examples are also possible.

Additionally or alternatively, the medical-support configuration of a given type of UAV may include one or more operational functions that are designed to provide or assist in medical support for the remote medical situation. For instance, a UAV may include wireless communication capabilities that allow remote medical personnel to assist those at the scene. For instance, a UAV might include in its package, a mobile phone or HMD, via which a bystander can communicate with and receive instructions from remote medical personnel, such that the bystander can be informed how to, e.g., provide care to a person who is injured or is suffering from a medical condition. As another example, a UAV may include program logic (e.g., medical support module(s) 516) that allows the UAV to perform certain diagnostic tests, in which the UAV analyzes data acquired from certain sensory systems of the UAV. Other examples are also possible.

In some embodiments, the selection of a UAV may be based, at least in part, on the particular person to whom medical support is going to be provided. For example, the medical-support system may determine that a particular user-account is associated with the medical situation. The medical-support system may then determine a service level for the particular user-account, and use the service level as a basis to select the UAV.

For example, there may be several UAVs that could be deployed to provide medical support in a particular medical situation. However, for various reasons, a particular one of the UAVs may only be deployed to someone who was paid for or otherwise is entitled to a higher service level. Accordingly, the particular UAV may only be selected if a person involved in the medical situation is authorized for the higher service level. Note that in some cases, the service level attributed to a particular communication may be that to which the person to whom the medical support is being provided by a UAV (e.g., the victim of an accident) is entitled. However, in other cases, the service level may be that of someone other than a person in need of medical care. For example, a family member, friend, or even a bystander to a medical situation, may have a particular service level that allows them to request medical support corresponding to the particular service level, on the behalf of another person in need.

The particular user-account may be determined in various ways. For example, a person may link their computing devices, such as their mobile phones, to a user-account for medical support. Accordingly, the medical-support system may determine an identification number for the remote device that provides the indication of the medical situation, and use the identification number to look up the associated medical-support user-account. Alternatively, the person who requests medical support may provide identification and/or log-in information, so that a medical-support user-account may be identified and/or verified by the medical-support system. Other techniques for determining the particular user-account are also possible.

In a further aspect, medical or other emergency history and/or other information related to the particular person in need of medical support may be utilized to select an appropriate UAV. For example, delivery of prescription medications by non-physicians may be strictly regulated, even in medical situations. To facilitate the verification and delivery of such medications, a medical-support system may include an opt-in registry, which includes persons' names and a list of medications for which each person has a current prescription. To facilitate diagnosis, the opt-in registry may further include a list of an individual's known medical conditions that may lead to medical care. In practice, a given user-account may indicate such prescription-authorization information, known medical conditions, and/or other medical information for the person. Accordingly, a medical-support system may access the user-account for a person in need of medical support to determine whether or not they have a prescription for a particular medication, such that a UAV including the particular medication can be dispatched.

D. Dispatching the Selected UAV

As noted above, block 608 of method 600 involves a medical-support system causing the selected UAV to travel to the target location to provide medical support, as shown by block

608. This function may be accomplished in various ways, depending upon the particular implementation.

In some embodiments, block 608 may simply involve a component of the medical-support system sending a message to another entity to indicate that the selected UAV should be deployed. For example, if method 600 is carried out by an access system 402, the access system may identify the medical situation, select an appropriate type of UAV, and send a message to the central dispatch system 408, which indicates that a UAV of the selected type should be dispatched to the target location. As another example, if method 600 is carried out by a central dispatch system 408, the central dispatch system may identify the medical situation, select an appropriate type of UAV, and send a message to the local dispatch system 408 that indicates that a UAV of the selected type should be dispatched to the target location. In either case, the central dispatch system 408 may then relay the message to the appropriate local dispatch system 410, which may operate a deployment system to launch the selected UAV.

In some embodiments, block 608 may involve one or more components of the medical-support system sending a message to instruct a deployment system to launch the selected UAV, or directly operating the deployment system to launch the selected UAV. Further, block 608 could involve one or more components of the medical-support system preparing the selected UAV to travel to the target location, such as by determining and setting way points to allow the UAV to navigate to the target location.

E. UAV Traveling to a Vicinity of the Remote Device

Referring now to the method 700 of FIG. 7, at block 702, the UAV travels to a nearby vicinity (e.g., within about 50 meters) of a target location of the medical situation. This target location can be a location of a remote device that requested medical support or of a remote device identified as a point-of-contact for the medical support.

For example, a remote device that requests medical support can identify another remote device as a point-of-contact for the medical support. Illustratively, a remote device may relay a request for medical support at a remote location and identify another remote device at the remote location as a point-of-contact for the medical support. The other remote device may be a cell phone and can be identified by the cell phone number, for example. Thus, the UAV can be controlled to travel to the remote location of the other remote device to communicate therewith and provide medical support.

Further, the target location can be updated, as needed, by communications between the remote device and the medical-support system. For example, the target location can be updated as the remote device is moved and/or as the location of the medical situation changes, such as if a person in need of medical support is being moved to another location.

F. UAV Communicating with the Remote Device

Once the UAV arrives at the vicinity of the target location, at block 704, the UAV communicates with the remote device. In one example, the UAV utilizes a short-range communication, e.g., Bluetooth, WiFi, NFC, ZigBee, short-range IR communications, RFID, etc., to identify the remote device and determine that the UAV is within the vicinity of the remote device.

The short-range communication may also include communications using sound and/or visible light. Illustratively, sound or visible light signals can be used to send relatively low bit rate information, such as a high, medium, or low urgency level of the medical situation. Generally, low bit rate information can be encoded in the sound or visible light signals using different patterns of frequencies or amplitudes, for example.

The above and other examples of short-range communications typically can be utilized with fewer electronic component requirements and less power consumption than other long-range communications, such as communications under the CDMA or LTE protocol or WiMAX. Further, remote devices, such as smartphones, typically include such short-range communication capabilities, e.g., for Bluetooth or WiFi networks, such that the UAV can communicate with the remote device using existing and available technology. Remote devices also typically include long-range communication capabilities but may be limited to a particular cellular service provider, which may have limited service at the location of the medical situation. Short-range communications can also be used to provide better security for the communications between the UAV and the remote device, as opposed to, long-range communications where data is typically transferred over long distances and perhaps more at risk of security breaches.

To identify the remote device, the UAV may detect a signal from the remote device and match a security key transmitted from the remote device to a predefined security key. If the security key matches the predefined security key, the UAV may proceed to provide medical support and can enable an otherwise restricted capability, as shown by block 706. If the security key does not match the predefined security key, then the UAV may refrain from traveling further, and may take other actions instead. For instance, the UAV might search for another signal with a matching security key, and, if none can be found, then alert the medical-support system that the remote device has not been located and/or return to the location of its deployment system, among other possibilities.

The UAV can identify the remote device using other processes, as well. In one non-limiting example, the UAV can send a message (such as a text message) and wait for a confirmation response message from the remote device. Thus, in this example, the message from the UAV can say "the UAV is above your location, please confirm" and a user can respond using the remote device and either confirm or deny that the UAV is above their location.

In yet another example, a short-range communication, such as an NFC or RFID system, can be utilized to require that the remote device be brought into close proximity with the UAV, perhaps within a few feet or even nearly touching. This type of short-range communication can further be utilized to confirm the identity of the remote device and to ensure that the UAV is at the correct location to provide medical support.

Further other handshaking processes can be performed between the UAV and the remote device to identify the remote device, define communication parameters, and establish communication channels for further communications between the UAV and the remote device.

G. Enabling Device and/or UAV Capability

Referring to block 706 of FIG. 7, various examples of the enabled or authorized capability are described herein, such as enabling an otherwise restricted communication capability, enabling any of the medical-support functionalities described above, or otherwise authorizing the UAV to provide medical support.

Generally, the otherwise restricted communication capability can include one or more of enabling wireless communications in a restricted bandwidth range, enabling wireless communications above a restricted power level or outside a restricted range, and/or granting access to a restricted communication network or protocol. In another example, a two-way short-range communication capability can be enabled between the remote device and the UAV. Illustratively, the UAV can serve as a local communication hot spot (e.g., a LAN node) and the UAV can grant access to the mobile device to connect to the communication hot spot and perhaps to a broader network to facilitate other communications that can be used to provide medical support.

In yet another example, the communication capability can include enabling the remote device to transmit a beacon signal that is detectable by the UAV to help the UAV determine the specific location of the medical situation. The beacon signal can be one or more of a radio frequency signal, a light signal, or an audio signal emitted by the mobile device. The beacon signal can then be used by the UAV to determine the location of the mobile device, which may correspond to the location of the medical situation or to a user of the device that can help direct the UAV to the location of the medical situation.

Further, authorizing the UAV to provide medical support can take many different forms, such as providing a package carried by the UAV (e.g., the package can include medicine, first aid items, medical devices, a mobile phone or HMD, etc.), providing information (e.g., medical support instructions), authorizing access to otherwise-restricted information (such as medical histories or other private or sensitive data, if the person or persons to whom such information relates have given permission for such access in a medical situation), or enabling some other operational function of the UAV.

In one example, the determination that the UAV is within a vicinity of the remote device is combined with identifying prescription information for a user of the remote device and then authorizing the UAV to provide the prescribed medication to the user. Numerous other examples are also possible.

Generally, the enabled or unlocked capability need not be of the remote device that requested the medical support but can be a capability of any other remote device, as well as, any other UAV. For example, the UAV can authorize use of a separate remote device, perhaps a mobile phone or HMD provided by the UAV itself. Thus, the UAV can provide access to specialized medical support through the separate remote device after confirming that the medical support is being provided to an authorized user.

In another example, the remote device can be authorized or enabled to utilize additional computing capabilities to facilitate the medical support. Illustratively, the remote device can be authorized or enabled to communicate with other computing devices, such as other mobile devices or a central server, and to utilize computing capabilities of these other computing devices to assist in the medical situation. These computing capabilities include processing capabilities and communication capabilities, among other examples. Thus, in one example, a remote device that requested medical support can communicate with other nearby mobile phones and can be authorized to use these other mobile phones as signal repeaters for communication purposes. Generally, these other computing devices (or users of such devices) can be asked to provide permission before granting access for the remote device to the computing capabilities.

In one scenario, a third party can request medical support for an injured individual. The medical situation may have occurred at a location with limited communication connectivity. In an example described briefly above, an injured individual may have fallen while hiking at the Grand Canyon and a third party (or notifier) may have had to leave the immediate location of the medical situation to seek higher ground to receive cell phone service. In this scenario, an medical-support system may dispatch a UAV to the location of the third party's remote device. Once the UAV arrives at a nearby vicinity of the remote device, the UAV can enable a short-range communication link with the remote device (e.g., the UAV can serve as a communication hot spot and allow the remote device to connect to another network through the UAV). The user of the remote device can then direct the UAV to the location of the injured individual and the remote device can be used to provide medical care instructions over the enabled communication link or otherwise utilize the communication link to provide support in the medical situation.

The functions of block 706 can also be performed or executed before the UAV arrives within the vicinity of the remote devices. For example, the medical-support system can authorize or enable an otherwise restricted capability after a request for medical support is received. In another example, the medical-support system can authorize or enable an otherwise restricted capability after a request for medical support is received and a UAV is dispatched to provide medical support.

In one scenario, a notifier uses a remote device to make a request for medical support. The medical-support system receives the request and dispatches a UAV to provide medical support, as described above. The medical-support system can then enable an otherwise restricted capability of the remote device. For example, the remote device can be authorized to use an otherwise restricted communication capability to facilitate communications between the remote device and the dispatched UAV. This communication capability can help the UAV identify and locate a remote device, which is at or near the location of the medical situation. Once the UAV arrives at the location of the remote device, another capability can be authorized, such as authorizing the UAV to provide further medical support. Consequently, in this example, a first capability can be authorized at or near the time that a request for medical support is made and a second capability can be authorized once a UAV arrives within a vicinity of the remote device. In this example, these first and second capabilities can be the same or different. Generally, the capability can be authorized or enabled for a limited time. Thus, for example, in response to a request for medical support, the medical-support system can enable a communication capability of a remote device for 30 minutes, for example. After the expiration of the time limit, the enabled capability may become restricted again or can be re-enabled, as needed.

VI. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

We claim:

1. A computer-implemented method comprising:
   identifying, by a computing device, a request for assistance at a remote emergency situation, wherein the request is associated with a remote device;
   identifying the remote device that is associated with the request for assistance;
   determining a target location corresponding to the emergency situation;
   controlling an unmanned aerial vehicle (UAV) to travel to the target location to provide emergency support; and
   enabling an otherwise restricted capability of one or more of the remote device or the UAV after controlling the UAV to travel to the target location, wherein the capability is a communication capability that is enabled to help provide emergency support in the remote emergency situation.

2. The method of claim 1, further comprising determining, via a short-range communication protocol, that the UAV is in a nearby vicinity of the remote device; and enabling another otherwise restricted capability of one or more of the remote device or the UAV in response to determining that the UAV is in the nearby vicinity of the remote device.

3. The method of claim 2, wherein determining that the UAV is in a nearby vicinity of the remote device comprises the UAV communicating with the remote device via the short-range communication protocol to determine that the UAV is within 50 meters of the remote device.

4. The method of claim 1, wherein the communication capability is a short-range, less than 50 meter, communication capability between the UAV and the remote device.

5. The method of claim 1, wherein the communication capability is emitting a beacon signal from the remote device, wherein the beacon signal is detectable by the UAV to determine a location of the remote device, and wherein the beacon signal is selected from the group consisting of a radio frequency signal, a light signal, and an audio signal.

6. The method of claim 1, wherein the communication capability is selected from the group consisting of communicating in an otherwise restricted bandwidth range, communicating above an otherwise restricted power level, and utilizing an otherwise restricted communication network or protocol.

7. The method of claim 1, wherein enabling the capability further comprises authorizing access to otherwise restricted information regarding one or more of a person identified by the remote device or the remote device itself.

8. The method of claim 1, wherein the request is received through a communication that originated from the remote device, wherein the method further comprises identifying the remote emergency situation based on information provided by the communication, and wherein the communication comprises at least one of: (a) a phone call, (b) a text-message, or (c) an electronic message generated by an application of the remote device.

9. The method of claim 1, wherein the UAV is selected from a plurality of UAVs that are configured to provide emergency support for a plurality of emergency situations, and wherein the selection of the UAV is based at least in part on a determination that the selected UAV is configured for the identified emergency situation.

10. The method of claim 1, wherein enabling the capability further comprises authorizing the UAV to provide assistance for the emergency situation.

11. The method of claim 10, wherein the authorized assistance is selected from the group consisting of providing information to assist in the emergency situation, providing an item to assist in the emergency situation, and enabling an operational function of the UAV to assist in the emergency situation.

12. The method of claim 1, wherein enabling the capability further comprises authorizing the remote device to request access to a computing capability of another device.

13. A non-transitory computer readable medium having stored therein instructions that are executable to cause a computing device to perform functions comprising:
   identifying a request for assistance at a remote emergency situation;
   identifying a remote device that is associated with the request for assistance;
   determining a target location corresponding to the emergency situation;
   controlling an unmanned aerial vehicle (UAV) to travel to the target location to provide emergency support;
   enabling an otherwise restricted capability of one or more of the remote device or the UAV after controlling the UAV to travel to the target location, wherein the capability is enabled to help provide emergency support in the remote emergency situation;
   determining, via a short-range communication protocol, that the UAV is in a nearby vicinity of the remote device; and
   enabling another otherwise restricted capability of one or more of the remote device or the UAV in response to determining that the UAV is in the nearby vicinity of the remote device.

14. The non-transitory computer readable medium of claim 13, wherein determining that the UAV is in a nearby vicinity of the remote device comprises controlling the UAV to communicate with the remote device to determine that the UAV is within 50 meters of the remote device.

15. The non-transitory computer readable medium of claim 13, wherein enabling at least one of the otherwise restricted capability or the other otherwise restricted capability comprises enabling an otherwise restricted communication capability.

16. The non-transitory computer readable medium of claim 13, wherein enabling at least one of the otherwise restricted capability or the other otherwise restricted capability comprises authorizing access to otherwise restricted information regarding one or more of a person identified by the remote device or the remote device itself.

17. The non-transitory computer readable medium of claim 13, wherein enabling at least one of the otherwise restricted capability or the other otherwise restricted capability comprises authorizing the UAV to provide assistance for the emergency situation.

18. An emergency-support system comprising:
   a plurality of unmanned aerial vehicles (UAVs), wherein the plurality of UAVs are configured to provide emergency support for a plurality of emergency situations; and
   at least one component that is configured to:
      identify a request for assistance at a remote emergency situation;
      identify a remote device that is associated with the request for assistance;
      determine a target location corresponding to the emergency situation;
      control at least one UAV of the plurality of UAVs to travel to the target location to provide emergency support;
      enable an otherwise restricted capability of one or more of the remote device or the UAV after controlling the UAV to travel to the target location, wherein the capability is enabled to help provide emergency support in the remote emergency situation; and
      enable access to otherwise restricted information regarding one or more of a person identified by the remote device or the remote device itself.

19. The emergency-support system of claim 18, wherein the at least one component is further configured to determine, via a short-range communication protocol, that the UAV is in a nearby vicinity of the remote device; and enable another otherwise restricted capability of one or more of the remote device or the UAV in response to determining that the UAV is in the nearby vicinity of the remote device.

20. The emergency-support system of claim 19, wherein the at least one component is further configured to control the UAV to communicate with the remote device to determine that the UAV is within 50 meters of the remote device.

21. The emergency-support system of claim 18, wherein the at least one component comprises a component of a UAV.

22. The emergency-support system of claim 18, wherein the at least one component is further configured to enable an otherwise restricted communication capability of one or more of the remote device or the UAV.

23. The emergency-support system of claim 18, wherein the at least one component is further configured to enable the UAV to provide assistance for the emergency situation.

* * * * *